US008367328B2

(12) United States Patent
Asada et al.

(10) Patent No.: US 8,367,328 B2
(45) Date of Patent: *Feb. 5, 2013

(54) METHOD FOR SYNTHESIZING DNA

(75) Inventors: Kiyozo Asada, Shiga (JP); Takashi Uemori, Otsu (JP); Yoshimi Sato, Shiga (JP); Tomoko Fujita, Takatsuki (JP); Kazue Miyake, Uji (JP); Osamu Takeda, Hikone (JP); Hiroyuki Mukai, Moriyama (JP); Ikunoshin Kato, Uji (JP)

(73) Assignee: Takara Bio Inc., Otsu-Shi (JP)

( * ) Notice: Subject to any disclaimer, the term of this patent is extended or adjusted under 35 U.S.C. 154(b) by 442 days.

This patent is subject to a terminal disclaimer.

(21) Appl. No.: 12/285,866

(22) Filed: Oct. 15, 2008

(65) Prior Publication Data

US 2009/0098613 A1 Apr. 16, 2009

Related U.S. Application Data

(63) Continuation of application No. 09/673,884, filed as application No. PCT/JP99/02121 on Apr. 21, 1999, now Pat. No. 7,521,178.

(30) Foreign Application Priority Data

Apr. 23, 1998 (JP) .................................. 10-114005
Nov. 6, 1998 (JP) .................................. 10-315243

(51) Int. Cl.
*C12Q 1/68* (2006.01)
*C12P 19/34* (2006.01)
*C07H 21/02* (2006.01)
*C07H 21/04* (2006.01)

(52) U.S. Cl. ...................... 435/6.1; 435/6.18; 435/91.2

(58) Field of Classification Search .................. None
See application file for complete search history.

(56) References Cited

U.S. PATENT DOCUMENTS

| | | | |
|---|---|---|---|
| 4,072,574 | A | 2/1978 | Loeb et al. |
| 5,153,181 | A | 10/1992 | Diringer et al. |
| 5,225,556 | A | 7/1993 | Barton |
| 5,418,162 | A | 5/1995 | Blakely et al. |
| 5,436,149 | A | 7/1995 | Barnes |
| 5,501,963 | A | 3/1996 | Burckhardt et al. |
| 5,554,498 | A | 9/1996 | Filler et al. |
| 5,556,772 | A | 9/1996 | Sorge et al. |
| 5,616,478 | A | 4/1997 | Chetverin et al. |
| 5,789,206 | A | 8/1998 | Tavtigian et al. |
| 5,795,722 | A | 8/1998 | Lacroix et al. |
| 5,917,031 | A | 6/1999 | Miura et al. |
| 5,928,906 | A | 7/1999 | Koster et al. |
| 6,008,025 | A | 12/1999 | Komatsubara et al. |
| 6,087,097 | A | 7/2000 | Persing |
| 6,168,922 | B1 | 1/2001 | Harvey et al. |
| 6,207,652 | B1 | 3/2001 | Sakai et al. |
| 6,348,336 | B1 | 2/2002 | Matveld et al. |
| 6,350,580 | B1 | 2/2002 | Sorge |
| 6,410,277 | B1 | 6/2002 | Barnes |
| 6,495,350 | B1 | 12/2002 | Lee et al. |
| 6,673,578 | B1* | 1/2004 | Uemori et al. ............... 435/91.2 |
| 2003/0092135 | A1 | 5/2003 | Peters |
| 2003/0118986 | A1 | 6/2003 | Merigan et al. |
| 2003/0143566 | A1 | 7/2003 | Helftenbein |
| 2003/0143600 | A1 | 7/2003 | Gocke et al. |
| 2003/0153028 | A1 | 8/2003 | Refseth et al. |

FOREIGN PATENT DOCUMENTS

| | | |
|---|---|---|
| CN | 1177008 A | 3/1998 |
| EP | 0 511 712 A1 | 11/1992 |
| EP | 0 745 687 A1 | 12/1996 |
| EP | 0 802 258 A2 | 10/1997 |
| EP | 0989192 A2 | 3/2000 |
| EP | 1 069 190 A2 | 1/2001 |
| EP | 1 111 044 A1 | 6/2001 |
| JP | 10-42874 A | 2/1998 |
| WO | WO-97/24444 A1 | 7/1997 |
| WO | WO-97/26896 A1 | 7/1997 |
| WO | WO-97/47208 A1 | 12/1997 |

OTHER PUBLICATIONS

Tsui, S. K.W. et al., Biotechnol. Lett., vol. 17, pp. 1-6 (1995).*
Jin, H.-J. et al., J. Appl. Physiol., vol. 9, pp. 383-388 (1997).*
Monteiro, L. et al., J. Clin. Microbiol., vol. 35, pp. 995-998 (1997).*
Peist, R. et al., Qiagen News, No. 3, pp. 7-9 (2001).*
Demeke, T. et al., Biotechniques, vol. 12, pp. 332-334 (1992).*
Furukawa, K. et al., Biochim. Biophys. Acta, vol. 740, pp. 466-475 (1983).*
Pandey, R.N. et al., Plant Mol. Biol. Rep., vol. 14, p. 17-22 (1996).*
Stratagene Catalog, p. 39 (1988).
Tigst, D. et al. Biotechniques, 1992, vol. 12, No. 3, pp. 332-334.
Suzanne C. et al., Proc. Natl. Acad. Sci. USA, 1994, vol. 91, No. 12, pp. 5695-5699.
Roman, J. et al., Biotechniques, 1997, vol. 23, No. 1, pp. 24-28.
Gunnar, T. et al., Methods Mol. Cel. Biol., 1995, vol. 5, No. 2, pp. 122-124.
Nagai et al., Biochemistry and Molecular Biology International, vol. 44, No. 1, pp. 157-163. (Jan. 1998).
Imamura et al., Biol. Pharm. Bull., vol. 18, No. 12, pp. 1647-1652 (Dec. 1995).

(Continued)

*Primary Examiner* — Teresa E Strelecka
(74) *Attorney, Agent, or Firm* — Birch, Stewart, Kolasch & Birch, LLP

(57) ABSTRACT

A DNA synthesis reaction-enhancer comprising at least one kind selected from the group consisting of acidic substances and cationic complexes; a DNA synthesis method in which during a DNA synthesis reaction a reaction is carried out in the presence of the above enhancer by using DNA polymerase; a DNA synthesis reaction composition comprising the above enhancer; a DNA synthesis reaction composition comprising two or more kinds of DNA polymerases each having 3'→5' exonuclease activity; a DNA synthesis method in which during a DNA synthesis reaction two or more kinds of DNA polymerases each having 3'→5' exonuclease activity are used; a kit for use in in vitro DNA synthesis, comprising two or more kinds of DNA polymerases each having 3'→5' exonuclease activity; and a kit for use in in vitro DNA synthesis, wherein the kit comprises the DNA synthesis reaction-enhancer and DNA polymerase. According to the present invention, DNA synthesis can be carried out at an efficiency more excellent as compared to conventional DNA synthesis reaction.

11 Claims, No Drawings

OTHER PUBLICATIONS

Uemori et al., Genes to Cells, vol. 2, pp. 499-512 (1997).
Ito et al., Nucleic Acids Research, vol. 19, No. 15, pp. 4045-4057 (1991).
Ishino et al., Journal of Bacteriology, vol. 180, No. 8, pp. 2232-2236 (Apr. 1998).
Jin et al., Journal of Applied Phycology, vol. 9, pp. 383-388 (1997).
Takahashi et al., "Enhancement of DNA Synthesis of Human Epithelial Carcinoma Cells by Acidic Fibroblast Growth Factor," Cell Structure and Function, vol. 14, pp. 121-128, 1989.
Beutler et al., "Interference of Heparin with the Polymerase Chain Reaction," BioTechniques, vol. 9, No. 2, pp. 166. (1990).
Wang et al. J. Clin. Microbiol., vol. 30, pp. 750-753 (1992).
Holodney et al. J.Clin. Microbiol., vol. 29, pp. 676-679 (1991).
Poli et al. PCR Meth. Appl., vol. 2, pp. 356-358 (1993).
Al-Soud et al. Applied Env. Microbiol., vol. 64, pp. 3748-3753, Oct. 1998.
Cline et al., "PCR fidelity of Pfu DNA polymerase and other thermostable DNA polymerases", Nucleic Acids Research, 1996, vol. 24, No. 18, pp. 3546-3551.
Takagi et al., "Characterization of DNA Polymerase from *Pyrococcus* sp. Strain KOD1 and Its Application to PCR", Applied and Environmental Microbiology, 1997, vol. 63, No. 11, pp. 4504-4510.
Perrino et al., "Hydrolysis of 3'-Terminal Mispairs in Vitro by the 3'->5' Exonuclease of DNA Polymerase ∂ Permits Subsequent Extension by DNA Polymerase α", Biochemistry, 1990, vol. 29, pp. 5226-5231.
Costa et al., "Polishing with T4 or Pfu polymerase increases the effeciency of cloning of PCR fragments", Nucleic Acids Research, 1994, vol. 22, No. 12, pp. 2423.
Sigma Catalog (1996) pp. 76, 268, 337, 338, 531, 532, 549, 550, 786, 864 and 1959.
"Heparin Sulphate" Wikipedia, en.wikipedia.org/wiki/Heparin-sulphate, Apr. 21, 2007.
Yang Shuqing et al., "Spontaneous enzymatic synthesis of DNA catalyzed by thermostable DNA polymerase", Institute of Genetics, Journal of Fudan University (Natural Science), vol. 34, No. 4, pp. 391-397, 1995.

* cited by examiner

METHOD FOR SYNTHESIZING DNA

This application is a Continuation of application Ser. No. 09/673,884 filed on Oct. 23, 2000, which issued as U.S. Pat. No. 7,521,178 on Apr. 21, 2009, and which is the national phase under 35 U.S.C. §371 of PCT International Patent Application No. PCT/JP99/02121 having an International filing date of Apr. 21, 1999, which also claims priority under 35 U.S.C. §119 to Patent Application No. JP 10-114005, filed on Apr. 23, 1998, and Patent Application No. JP 10-315243, filed on Nov. 6, 1998, the entire contents of which are hereby incorporated by reference.

TECHNICAL FIELD

The present invention relates to a DNA synthesis reaction-enhancer, a DNA synthesis method, a DNA synthesis reaction composition and a kit usable for the DNA synthesis method, which are useful in the field of genetic engineering.

BACKGROUND ART

The DNA synthesis is employed for various purposes in the research of the field of genetic engineering. Almost all of them, except for synthesis of short chain DNA such as oligonucleotides, are carried out by the enzymatic method utilizing DNA polymerase. Accordingly, the DNA polymerase is highly valuable for reagents for DNA sequencing, DNA labelling, or site-directed mutagenesis. In addition, recently, thermostable DNA polymerases have been remarked with the developments of the polymerase chain reaction (PCR) method and the reverse transcription-PCR(RT-PCR) in which the PCR method and the reverse transcriptase reaction are combined. Therefore, various kinds of DNA polymerases suitable for PCR method mentioned above have been developed, and commercialized.

The presently known DNA polymerases can be roughly classified by amino acid sequence homology into four families, among which Family A (pol I type enzymes) and Family B (α-type enzymes) account for the great majority. Although the DNA polymerases belonging to the respective families possess generally similar biochemical properties, detailed comparison reveals that depending upon individual enzymes, each of the DNA polymerases has different properties for substrate specificity; substrate analog-incorporating efficiency; degree and rate for primer extension; mode of DNA synthesis; presence or absence of exonuclease activity; optimum reaction conditions such as temperature and pH, and sensitivity against inhibitors. Therefore, the enzyme best suited for the application has so far been selected from the available DNA polymerases.

For example, *Pyrococcus furiosus*, a hyperthermophilic archaebacterium, produces DNA polymerase belonging to α-type, and the gene thereof has been isolated [*Nucleic Acids Research* 21, 259-265 (1993)]. Recently, novel DNA polymerase showing no structural similarity to any known DNA polymerase was found in the above bacterial strain. In this DNA polymerase, two novel proteins form a complex, whereby exhibiting DNA polymerase activity. In addition, the novel DNA polymerase exhibits potent 3'→5' exonuclease activity and excellent primer extension activity. For example, when the enzyme is used for PCR, a DNA fragment of a size of about 20 kb can be amplified.

On the other hand, in DNA synthesis reaction using DNA polymerase, it is important to set appropriate reaction conditions, as well as to select an appropriate enzyme. Major conditions for reaction include reaction mixture composition, pH, reaction temperature, and template and primer concentration. In addition, these reaction conditions must be set in accordance with the enzyme used and the purpose. However, such settings may be difficult to make in some cases.

In addition, there has been known that efficient DNA synthesis can be carried out by using a combination of plural DNA polymerases, wherein the efficient DNA synthesis could not be achieved by single DNA polymerase [*Proc. Natl. Acad. Sci. USA* 91, 5695-5699 (1994)]. The method is a method using in PCR a mixture of DNA polymerase having 3'→5' exonuclease activity (for example, the above *Pyrococcus furiosus*-derived α-type DNA polymerase) and DNA polymerase not having such an activity (for example, *Thermus aquaticus*-derived DNA polymerase (Taq DNA polymerase), and is known as LA-PCR method. According to this method, there are exhibited such effects that the yield of amplified DNA is increased, as compared with that of conventional PCR using only one kind of DNA polymerase, and that long chain length of DNA which could not be amplified by conventional PCR can be amplified. However, such effects are only exhibited when an enzyme having 3'→5' exonuclease activity is used in combination with an enzyme having no such activity.

As described above, the DNA synthesis reaction using DNA polymerase is indispensable as a genetic engineering procedure. Moreover, it is important to increase their efficiency for research or the like. However, a presently available reaction system has a defect in that it is not sufficiently optimized to be utilized for research or the like. For this reason, there has been a demand for a method enabling more efficient DNA synthesis as compared to that of the conventional DNA synthesis reactions.

DISCLOSURE OF INVENTION

The present invention has been accomplished in view of the prior art described above, and an object of the present invention is to provide (1) a DNA synthesis reaction-enhancer; (2) a DNA synthesis method characterized in that the reaction is carried out in the presence of the DNA synthesis reaction-enhancer; (3) a DNA synthesis reaction composition comprising the DNA synthesis reaction-enhancer; (4) a DNA synthesis reaction composition comprising two or more kinds of DNA polymerases each having 3'→5' exonuclease activity; (5) a DNA synthesis method characterized in that during the DNA synthesis reaction two or more kinds of DNA polymerases each having 3'→5' exonuclease activity is used; (6) a kit comprising two or more kinds of DNA polymerases each having 3'→5' exonuclease activity; and (7) a kit comprising the DNA synthesis reaction-enhancer and DNA polymerase.

As a result of intensive studies, the present inventors have found that efficiency of the DNA synthesis reaction by DNA polymerase is improved in the coexistence of at least one kind selected from the group consisting of acidic substances and cationic complexes. In addition, they have found that extremely efficient DNA synthesis is generated when two or more kinds of DNA polymerases each having 3'→5' exonuclease activity are mixed. Further, excellent gene amplification reaction system is constructed by combination of these techniques, thereby completing the present invention.

Concretely, the gist of the present invention relates to:

[1] a DNA synthesis reaction-enhancer comprising at least one kind selected from the group consisting of acidic substances and cationic complexes;

[2] a DNA synthesis method characterized in that during a DNA synthesis reaction a reaction is carried out in the presence of the DNA synthesis reaction-enhancer of item [1] above by using DNA polymerase;

[3] a DNA synthesis reaction composition comprising the DNA synthesis reaction-enhancer of item [1] above;

[4] a DNA synthesis reaction composition comprising two or more kinds of DNA polymerases each having 3'→5' exonuclease activity;

[5] a DNA synthesis method characterized in that during a DNA synthesis reaction two or more kinds of DNA polymerases each having 3'→5' exonuclease activity are used;

[6] a kit for use in in vitro DNA synthesis, comprising two or more kinds of DNA polymerases each having 3'→5' exonuclease activity; and

[7] a kit for use in in vitro DNA synthesis, wherein the kit comprises the DNA synthesis reaction-enhancer of item [1] above and DNA polymerase.

BEST MODE FOR CARRYING OUT THE INVENTION (I) DNA Synthesis Reaction-Enhancer of the Present Invention One of the great features of the present invention resides in that the DNA synthesis reaction-enhancer comprises at least one kind selected from the group consisting of acidic substances and cationic complexes. The DNA synthesis reaction-enhancer of the present invention can exhibit an action of enhancing DNA synthesis reaction by DNA polymerase, owing to contain at least one kind (active ingredient) selected from the group consisting of acidic substances and cationic complexes.

The term "DNA synthesis reaction-enhancer" of the present invention refers to the acidic substance or cationic complex mentioned above alone, or a mixture comprising both the acidic substance and cationic complex, each of which is capable of exhibiting an action of enhancing DNA synthesis reaction. In addition, as to the term "DNA synthesis reaction-enhancer" of the present invention, when a complex of an acidic substance and a cationic complex is formed, such a complex is also encompassed therein, as long as the substance is capable of exhibiting an action of enhancing DNA synthesis reaction by DNA polymerase.

Furthermore, mixtures in which various additives are supplemented within the range so that the mixture can exhibit the action of enhancing DNA synthesis reaction by DNA polymerase are also encompassed in the "DNA synthesis reaction-enhancer" of the present invention.

The term "action of enhancing DNA synthesis reaction" can be examined by the chain length of new synthetic DNA chain per unit time or by the amount of amplified product in PCR per unit time. In addition, the action can also be examined by comparing an activity where at least one kind selected from the group consisting of acidic substances and cationic complexes is added with an activity where at least one kind selected from the group consisting of acidic substances and cationic complexes is not added, when determining DNA polymerase activity, for instance, when determining an incorporation of labeled nucleotide into the new synthetic DNA chain. Such an "action of enhancing DNA synthesis reaction" encompasses an action of improving efficiency for synthesis reaction.

It is thought that the action of the DNA synthesis reaction-enhancer of the present invention is in, for example, but are not particularly limited to, that the DNA synthesis reaction-enhancer acts as a DNA polymerase activity-enhancer on DNA polymerase, thereby improving its catalytic activity; or that nonspecific interaction of the enzyme on template DNA is suppressed by retaining DNA polymerase on a molecule of the active ingredient of the above DNA synthesis reaction-enhancer, to provide the enzyme in the optimum amount for template DNA; and in addition that the DNA synthesis reaction-enhancer acts on template DNA so as to keep its steric structure so that the DNA synthesis reaction is easily progressed, thereby efficiently exhibiting the activity of the DNA polymerase. In addition, it is thought that another embodiment for the action of the DNA synthesis reaction-enhancer of the present invention is in the improvement of the efficiency of annealing for template DNA and primers.

The acidic substances used in the DNA synthesis reaction-enhancer mentioned above are substances having an action of enhancing DNA synthesis reaction as DNA polymerase activity-enhancers, and concretely include negatively charged substances or salts thereof, especially acidic substances or salts thereof.

In the DNA synthesis reaction-enhancer of the present invention, a DNA synthesis reaction can be enhanced by optimizing the interaction between DNA polymerase and template DNA, which increases with the progress of the DNA synthesis reaction, when an acidic substance is used.

The acidic substances having an action of enhancing DNA synthesis reaction include, for example, but are not particularly limited to, acidic polymer substances such as acidic polysaccharides. In addition, there can be used polyvinyl sulfates, polystyrene sulfates, polyglutamic acids, polyacrylic acids, DNAs not functioning as templates (i.e., DNAs not serving as templates for synthesis of subject DNA), and the like. In the present specification, the term "acidic substance" also encompasses salts thereof. The acidic polysaccharides include, for example, sulfate group-containing sulfated polysaccharides, representatively exemplified by sulfated-fucose-containing polysaccharides, dextran sulfate, carrageenan, heparin, heparan sulfate, rhamnam sulfate, chondroitin sulfate, dermatan sulfate, and the like, and polyuronic acids such as hyaluronic acid, alginic acid and pectin. In addition, as the sulfated-fucose-containing polysaccharides, there can be used, for example, sulfated-fucose-containing polysaccharide-F or sulfated-fucose-containing polysaccharide-U. The term "sulfated-fucose-containing polysaccharide-F" as used herein refers to a sulfated-fucose-containing polysaccharide substantially contains no uronic acid, obtainable from brown algae or the like by the method, for instance, described in WO 97/26896 or WO 97/47208. In addition, the term "sulfated-fucose-containing polysaccharide-U" refers to a sulfated-fucose-containing polysaccharide containing uronic acid, obtainable by the methods described in the above publications.

The salts of the acidic substances described above are not particularly limited, as long as they have an action of enhancing DNA synthesis reaction, with preference given to water-soluble salts. For example, there are included alkali metal salts such as sodium dextran sulfate, sodium alginate, sodium polyglutamates, sodium polystyrene sulfates, heparin sodium, potassium polyvinyl sulfates, potassium dextran sulfate and heparin lithium.

The acidic substances mentioned above may be those isolated and purified from naturally occurring substances or chemically or enzymatically synthesized products, as long as they maintain an action of enhancing DNA synthesis reaction. In addition, the acidic substances described above may be unpurified or partially purified products containing the acidic substances. Furthermore, the acidic substances described above may be appropriately modified, as long as the action of enhancing DNA synthesis reaction is maintained. In addition, the acidic substances described above may be substances obtained by degradation procedures so as to have appropriate molecular weights, or those obtained by carrying out molecular weight fractionation after such degradation procedures, as long as these substances have an action of enhancing DNA synthesis reaction. In the present invention, acidic substances having a molecular weight of several thousands or more can be preferably used. Furthermore, these substances may be used singly or in admixture of two or more kinds.

The cationic complexes used for the DNA synthesis reaction-enhancer of the present invention may be any substances, as long as they have an action of enhancing DNA synthesis reaction of DNA polymerase, and concretely include positively charged complexes or salts thereof, especially complex cations or complex salts thereof.

In the DNA synthesis reaction-enhancer of the present invention, when a cationic complex is used, the efficiency for annealing between template DNA and primers can be increased, and as a result, the DNA synthesis reaction can be enhanced. In addition, desired amplified fragments can be obtained even under conditions that have been difficult in DNA amplification, even under conditions of, for example, low magnesium concentrations, low primer concentrations, low enzyme amounts, amplification of GC-rich regions, and the like. Furthermore, when the above cationic complex is used, amplification can be enhanced even in PCR for long-chain DNA.

In addition, the DNA synthesis reaction can be further enhanced by combining the acidic substances and cationic complexes mentioned above.

The cationic complexes having an action of enhancing DNA synthesis reaction are not particularly limited, and there can be used, for instance, transition metal complexes. In the present specification, the term "cationic complex" also encompasses salts thereof.

The transition metal complex may be any complex capable of exhibiting an action of enhancing DNA synthesis reaction, and complexes having as the central atom a transition element in Group VIII of the Periodic Table (Kagaku Jiten, 1st edition, Tokyo Kagaku Dojin) are preferred. The above Group VIII transition element includes, but not particularly limited, as long as it forms a complex capable of exhibiting an action of enhancing DNA synthesis reaction, for instance, cobalt (Co), rhodium (Rh), iridium (Ir) and the like. In addition, the ligands in the complex include, but not particularly limited to, monodentate ligands, bidentate ligands, tridentate ligands, and tetradentate ligands. For example, neutral ligands such as $H_2O$, $NH_3$, CO, NO and pyridine, and chelate ligands such as $H_2NCH_2CH_2NH_2$ may be exemplified. In addition, the complex may contain as a ligand an anionic ligand, for instance, $Cl^-$, $OH^-$, $NO_2^-$, $CN^-$, $CO_3^-$, or the like, as long as it is a cationic complex capable of being present as a complex cation in the reaction mixture. The kinds of ligands in the above complex may be one kind or a plural kinds. Furthermore, as to cationic complexes, there exist geometric isomers, optical isomers and linkage isomers, and any cationic complexes are included in the DNA synthesis reaction-enhancer of the present invention, as long as they have an action of enhancing DNA synthesis reaction.

Concrete examples of the transition metal complex include, for instance, $[Co(NH_3)_6]Cl_3$, $[Co(H_2NCH_2CH_2NH_2)_3]Cl_3$, $[Co(NH_3)_5(H_2O)]Cl_3$, $[Co(H_2O)(NH_3)_5]_2(SO_4)_3$, $[Co(OH)(NH_3)_5]Cl_2$, $[Rh(H_2NCH_2CH_2NH_2)_3]Cl_3$, $[Rh(NH_3)_6]Br_3$, $[Rh(NH_3)_5(H_2O)]Cl_3$, $[RhCl_2(NH_3)_4]Cl$, $[Ir(NH_3)_6]Cl_3$, $[IrCl(NH_3)_5]Cl_2$, $[Ir(H_2NCH_2CH_2NH_2)_3]I_3$, and the like. Among the above-mentioned transition metal complexes, especially one or more kinds selected from the group consisting of $[Co(NH_3)_6]Cl_3$, $[Co(H_2NCH_2CH_2NH_2)_3]Cl_3$ and $[Rh(H_2NCH_2CH_2NH_2)_3]Cl_3$ are preferable.

The salts of the cationic complexes described above are not particularly limited, as long as they have an action of enhancing DNA synthesis reaction, with preference given to water-soluble salts. For example, there are included salts of halogenides such as chlorides; salts of inorganic acids such as sulfates; and salts of organic acids such as acetates. In other words, even salts of the acidic substance and cationic complex of the DNA synthesis reaction-enhancer of the present invention can be preferably used, as long as they ionize in the reaction mixture.

The cationic complex mentioned above may, for example, be any substance, as long as it maintains an action of enhancing DNA synthesis reaction. In addition, the cationic complex described above may be an unpurified or partially purified product containing the complex. Furthermore, the cationic complex may be appropriately modified within a range in which an action of enhancing DNA synthesis reaction is maintained. Furthermore, these substances can be used singly or in admixture.

The DNA polymerase used for DNA synthesis reaction which is enhanced by the DNA synthesis reaction-enhancer of the present invention is not particularly limited, and includes, for instance, pol 1-type DNA polymerases [*E. coli* DNA polymerase I, Klenow fragment, *Thermus aquaticus*-derived DNA polymerase (Taq DNA polymerase), and the like], α-type DNA polymerases [the above-mentioned α-type *Pyrococcus furiosus*-derived DNA polymerase, *Thermococcus litralis*-derived DNA polymerase (VENT DNA polymerase), *Pyrococcus* sp.-derived DNA polymerase (Pyrobest DNA polymerase, KOD DNA polymerase), *Pyrococcus* sp.-derived DNA polymerase GB-D (DEEP VENT DNA polymerase), and the like], and non-α, non-poll type DNA polymerases not belonging to any of these polymerases. Incidentally, each of the poll type DNA polymerases and α-type DNA polymerases refers to a group of enzymes classified by the homology on the amino acid sequences thereof, and the feature on the amino acid sequences is described in *Nucleic Acids Research* 15, 4045-4057 (1991).

In addition, the non-α, non-pol I type DNA polymerases include, for example, DNA polymerase derived from *Pyrococcus furiosus* described in WO 97/24444. In the present specification, for the sake of distinguishing between the above non-α, non-pol I type DNA polymerase derived from above-mentioned *Pyrococcus furiosus* and the α-type DNA polymerase, which is similarly produced by *Pyrococcus furiosus*, the non-α, non-pol I type DNA polymerase is referred to as Pfu DNA Polymerase II. In addition, the α-type DNA polymerase derived from the above-mentioned *Pyrococcus furiosus* is referred to as Pfu DNA Polymerase I.

Pfu DNA Polymerase II is an enzyme having the properties shown below.

Properties of Pfu DNA Polymerase II:

1) Exhibiting higher activity when polymerase activity is determined for a case of using as the substrate a complex formed by annealing primers to single-stranded template DNA than that of a case of using activated DNA as the substrate;

2) Having 3'→5' exonuclease activity;

3) Capable of amplifying DNA fragments of about 20 kilo base pairs without addition of another enzyme when polymerase chain reaction (PCR) is carried out with λDNA as a template under the following conditions:

Conditions for PCR:
(a) Composition for Reaction Mixture: Comprising 10 mM Tris-hydrochloric acid (pH 9.2), 3.5 mM magnesium chloride, 75 mM potassium chloride, 0.4 mM each of dATP, dCTP, dGTP and dTTP, 0.01% bovine serum albumin, 0.1% Triton X-100, 5.0 ng/50 µl of λDNA, and 10 pmole/50 µl of primer λA (SEQ ID NO: 1 in Sequence Listing) and primer λB (SEQ ID NO: 2 in Sequence Listing), and 3.7 U/50 µl of DNA polymerase;
(b) Reaction Conditions: PCR is carried out in 30 cycles, wherein one cycle of reaction comprises a process consisting of 98° C., 10 seconds—68° C., 10 minutes.
4) Constituted by two kinds of DNA polymerase-constituting proteins corresponding to about 90,000 Daltons and about 140,000 Daltons on SDS-PAGE.

In addition, the gene encoding the above Pfu DNA Polymerase II has been already cloned, and *Escherichia coli* JM109 transformed with plasmid pFU1001 carrying the gene is named and identified as *Escherichia coli* JM109/pFU1001, and deposited under the accession number of FERM BP-5579 with the National Institute of Bioscience and Human-Technology, Agency of Industrial Science and Technology, Ministry of International Trade and Industry, of which the address is 1-3, Higashi 1-chome, Tsukuba-shi, Ibaraki-ken (Zipcode 305-8566), Japan, since Aug. 11, 1995 (date of original deposit). Therefore, the transformant is cultured, and Pfu DNA polymerase II mentioned above can be obtained from the resulting culture by, for example, the method described in WO97/24444 (pages 28-29, Example 3).

In DNA synthesis reactions using various kinds of DNA polymerases described above, the efficiency of DNA synthesis of the DNA polymerases is surprisingly increased by adding the DNA synthesis reaction-enhancer of the present invention to the reaction mixture. In this case, DNA synthesis efficiency increases similarly when using two or more kinds of DNA polymerases, for instance, two or more kinds of DNA polymerases each having 3'→5' exonuclease activity (for instance, α-type DNA polymerase and non-α, non-pol I type DNA polymerase), or one DNA polymerase having 3'→5' exonuclease activity and the other DNA polymerase having no 3'→5' exonuclease activity.

For example, the amount of amplified product increases, when PCR is carried out by using a reaction mixture supplemented with the DNA synthesis reaction-enhancer of the present invention, in comparison to one obtained by carrying out PCR without this addition. For example, an amplified product can be obtained by the addition of the DNA synthesis reaction-enhancer of the present invention, even under conditions that have conventionally been difficult in amplification. In addition, the amount of amplified product can be quantified by, for example, subjecting a given amount of the reaction mixture after PCR to electrophoresis, staining the gel after electrophoresis with ethidium bromide or the like, and determining the fluorescence intensity of the band ascribed to the amplified product by means of an imaging analyzer or the like. When the amount of amplified product is quantified as described above and comparison is made between one in which PCR is carried out by using a reaction mixture added with the DNA synthesis reaction-enhancer of the present invention and one in which PCR is carried out without such addition, the amount of amplified product shows an increase by about 2 to 5 folds, though the level of increase depends on length of a product to be amplified, GC content, and the like, in comparison with those. In addition, efficient DNA amplification is also possible from a small amount of template DNA.

Furthermore, in PCR using the DNA synthesis reaction-enhancer of the present invention, the reaction time period required for obtaining the same amount of amplified product is shorter as compared to that of conventional PCR.

Generally in PCR, DNA amplification is carried out by three steps of dissociation (denaturation) of double stranded template DNA to single stranded one; annealing of a primer to single stranded template DNA, a complementary strand synthesis (extension) from the primer. In addition, DNA amplification is also carried out in a so-called "shuttle PCR" ["PCR Hou Saizensen (PCR Method Frontier)," '*Proteins, Nucleic Acids and Enzymes*' an extra number 41, No. 5, 425-428 (1996)], which is a two-step reaction, in which among the three-step reactions described above, the annealing step and the extension reaction step of the primer are carried out at the same temperature. The DNA synthesis reaction-enhancer of the present invention can particularly shorten the time period required for the above extension step, the time period required for an entire synthesis reaction can be shortened, in either of the above-mentioned three-step reaction and two-step reaction.

Here, the reaction time required for obtaining the same amount of amplified product by conventional PCR can be evaluated by, for example, using as a standard the amount of amplified product when PCR is carried out by using a reaction mixture supplemented with the DNA synthesis reaction-enhancer of the present invention. In other words, the reaction time period can be determined by sampling a reaction mixture for each cycle of PCR, wherein the PCR is carried out without the addition of the above enhancer; quantifying the amount of amplified product as described above; determining the number of cycles until reaching the same amount as the amplified amount obtained in the presence of the DNA synthesis reaction-enhancer of the present invention; and calculating the reaction time period from the number of cycles and the time period needed per one cycle. In addition, the time period needed per one cycle of PCR using the DNA synthesis reaction-enhancer of the present invention can be set to be shorter than the time period needed per one cycle of ordinary PCR. The time period needed per one cycle, in the case of 3-step reactions, for example, can be obtained as the sum of the retention time periods for each step of denaturation, primer annealing, and primer extension, and the time period for reaching each set temperatures from denaturation to primer annealing, from primer annealing to primer extension, and from primer extension to denaturation in the next cycle. In 2-step reactions, the time period needed per one cycle can be obtained as the sum of the retention times for each step and the transition time period between steps. When comparison is made between the total time period needed for the PCR to be carried out using a reaction mixture supplemented with the DNA synthesis reaction-enhancer of the present invention and the total time period needed for PCR to be carried out without the addition, the total time period needed can be shortened to about ½, which may vary depending on a length of a fragment to be amplified, GC content, and the like.

Since the DNA synthesis reaction-enhancer of the present invention can shorten the time period required for the entire amplification reaction, there can be exhibited an excellent effect that gene diagnostic method or the like can be performed in shorter time periods by using the enhancer for gene diagnostic method or the like on the basis of PCR method.

(II) DNA Synthesis Reaction Composition of the Present Invention

As an embodiment, the DNA synthesis reaction composition of the present invention includes, for instance, a composition comprising the DNA synthesis reaction-enhancer described in the above item (I). The above composition may comprise various components necessary for DNA synthesis using DNA polymerase, for example, dNTP, magnesium chloride and buffer components for maintaining appropriate pH. The composition may further comprise DNA polymerase.

The DNA polymerase contained in the DNA synthesis reaction composition is not particularly limited, and includes various kinds of DNA polymerases described in the above item (I). The DNA synthesis reaction composition may contain one kind of enzyme or may contain two or more kinds of (plural kinds of) enzymes. For example, when a plurality of DNA polymerases are contained, the DNA polymerase may be the combination of DNA polymerase having 3'→5' exonuclease activity used for LA-PCR and DNA polymerase having no such activity mentioned above. In addition, the DNA synthesis reaction composition of the present invention comprising thermostable DNA polymerase is suitable for synthesis of DNAs having nucleotide sequences which easily form higher order structures and the use for PCR.

In addition, another embodiment of the DNA synthesis reaction composition of the present invention includes a composition comprising two or more kinds of DNA polymerases each having 3'→5' exonuclease activity. The above composition may also comprise various components necessary for DNA synthesis as described above and/or the DNA synthesis reaction-enhancer mentioned above.

As a composition comprising a plurality of DNA polymerases, compositions utilized in LA-PCR method have been conventionally known. As described above, a composition utilized for LA-PCR method is prepared by combining a DNA polymerase having 3'→5' exonuclease activity and a DNA polymerase having no such activity or exhibiting no such activity.

The term "having 3'→5' exonuclease activity" as used herein means that the 3'→5' exonuclease activity owned by naturally occurring DNA polymerase has not been removed or reduced by a chemical method or genetic engineering method, i.e., the activity is substantially owned. In addition, the term "DNA polymerase exhibiting no 3'→5' exonuclease activity" refers to a DNA polymerase of which 3'→5' exonuclease activity has been removed or reduced by a chemical method or genetic engineering method.

The present inventors have clarified that when DNA polymerases each having 3'→5' exonuclease activity are combined, surprisingly, DNA synthesis reaction can be accomplished at higher reaction rates than those by LA-PCR method.

Such compositions include, for instance, but are not particularly limited to, a composition comprising a combination of thermostable DNA polymerase belonging to the α-type and thermostable DNA polymerase belonging to the non-α, non-pol I type. In addition, the performance of the above composition is improved by the addition of the DNA synthesis reaction-enhancer described above.

One of the features of the above composition resides in that the DNA synthesizing rate per unit time is very high. When the above composition is used for PCR method, the time period needed for amplifying DNA of the same chain length is shorter than that for conventional PCR method and LA-PCR method. Therefore, DNA amplification can be carried out even under PCR conditions that were impossible for DNA amplification by conventional methods.

Since the DNA synthesis reaction composition of the present invention can shorten the time period needed for an entire amplification reaction, there is exhibited an excellent effect that gene diagnostic method or the like can be performed in shorter time periods by using the composition, for instance, for genetic diagnostic method or the like on the basis of PCR method.

(III) DNA Synthesis Method of the Present Invention

According to the use of the DNA synthesis reaction-enhancer of the present invention or the DNA synthesis reaction composition of the present invention, a DNA synthesis reaction can be carried out at higher efficiency than that of conventional method by preparing a reaction mixture. For example, when the DNA synthesis method of the present invention is used for PCR method, an amplified product can be obtained with shorter reaction time than conventional PCR method or LA-PCR method.

Embodiments for the DNA synthesis method of the present invention include a method using two or more kinds of DNA polymerases; a method using DNA polymerase having 3'→5' exonuclease activity and DNA polymerase having no such activity; a method using two or more kinds of DNA polymerases each having 3'→5' exonuclease activity; and a method using α-type DNA polymerase and non-α, non-pol I type DNA polymerase. Further, there is included a method in which the DNA synthesis method mentioned above is carried out by PCR method.

According to the DNA synthesis method of the present invention, since the time period needed for an entire amplification reaction can be shortened, there can be exhibited an excellent effect that gene diagnostic method or the like can be performed in shorter time periods by using the method for gene diagnostic method or the like on the basis of PCR.

In addition, the DNA synthesis method of the present invention can also be utilized for such procedures utilizing DNA polymerases as DNA labeling and nucleotide sequencing by the dideoxy method.

(IV) Kits for DNA Synthesis Method of the Present Invention

DNA can be synthesized more conveniently and efficiently by using the kit of the present invention. The kit is not particularly limited, as long as the kit is usable for reactions involving DNA synthesis, and includes kits for DNA synthesis reactions in vitro. Concrete examples include kits for DNA nucleotide sequencing by the dideoxy method, kits for DNA labeling, kits for PCR, kits for cDNA synthesis, and kits for site-directed mutagenesis.

One of the great features of the kit of the present invention resides in that the kit comprises the DNA synthesis reaction-enhancer of the present invention and/or two or more kinds of DNA polymerases each having 3'→5' exonuclease activity. In other words, an embodiment includes a kit comprising the DNA synthesis reaction-enhancer of the present invention, and another embodiment includes a kit comprising two or more kinds of DNA polymerases each having 3'→5' exonuclease activity. Furthermore, the present invention also encompasses a kit comprising both the DNA synthesis reaction-enhancer of the present invention and the two or more kinds of DNA polymerases each having 3'→5' exonuclease activity.

The DNA synthesis reaction enhancers include at least one kind selected from the group consisting of acidic substances and cationic complexes described in the above item (I). The two or more kinds of DNA polymerases each having 3'→5' exonuclease activity include, for instance, α-type DNA polymerase and non-α, non-pol I type DNA polymerase, the polymerases preferably being thermostable DNA polymerases. The kit comprising the DNA synthesis reaction-enhancer of the present invention further comprises one kind or two or more kinds of appropriate DNA polymerases, with particular preference given to thermostable DNA polymerases. This kit may also comprise reagents necessary for DNA polymerase reactions, such as dNTP, magnesium chloride, and buffer components for keeping the reaction mixture at appropriate pH, in any of the embodiments.

The DNA synthesis reaction-enhancer mentioned above and DNA polymerases may be contained in the kit in the form of single components, or in the form added to the reaction buffer or the like.

Since the DNA synthesis reaction using the kit of the present invention allows to give a very large amount of DNA synthesized per unit time period than that of ordinary reaction systems, there is exhibited an excellent effect that the time period needed for the procedures can be shortened when applied to various kinds of procedures involving DNA synthesis reactions, representatively exemplified by DNA labeling, PCR, cDNA synthesis, and site-directed mutagenesis. For example, when this kit is applied to PCR, the time period needed for amplifying a DNA of the same chain length is shorter than that of conventional PCR method and LA-PCR method. Therefore, DNA amplification can be carried out even under PCR conditions that were impossible for DNA amplification by conventional methods. In addition, the kit of the present invention can shorten the time period needed for an entire amplification reaction, there is exhibited an excellent effect that gene diagnostic method or the like can be performed in shorter time periods by using the kit for gene diagnostic method or the like on the basis of PCR method.

In addition, the kit of the present invention is utilized to amplify nucleic acids by PCR method, so that there is exhibited an excellent effect that the time period needed for an entire amplification reaction can be shortened, or that the yield of the product obtained by the amplification reaction can be improved. In this case, a reaction mixture for amplification is prepared by mixing reagents necessary for PCR contained in the kit, and at least one kind selected from the group consisting of acidic substances and cationic complexes is added to the reaction mixture. Thereafter, a reaction in cycles is carried out in which each of denaturation, annealing, and extension processes is repeated. At least one kind selected from the group consisting of acidic substances and cationic complexes is added in an amount effective for shortening the reaction time period and/or for increasing the yield of the amplified product. Furthermore, in PCR method utilizing the kit of the present invention, there is exhibited an excellent effect that the chain length of the fragment amplified is made longer, in comparison to that obtained by PCR method not utilizing the kit of the present invention.

The reaction mixture mentioned above comprises the following components: 1) a nucleic acid serving as a template, 2) an appropriate reaction buffer, 3) DNA polymerase, 4) dATP, dTTP, dGTP and dCTP, and 5) at least one oligonucleotide primer. At least one kind selected from the group consisting of acidic substances and cationic complexes may be added in an effective amount to the reaction mixture after preparation, or may be added as a component of the reaction buffer.

According to the present invention, there is exhibited an excellent effect gene diagnostic method or the like can be performed in shorter time periods by the use for gene diagnostic method or the like on the basis of PCR, which involves the handling of a large number of samples.

The present invention will be hereinbelow described in further detail by means of the working examples, without intending to restrict the scope of the present invention to these working examples.

In the following working examples, the activities of the commercially available enzymes were shown on the basis of the indication for each enzyme, provided that the enzyme activity unit for Pfu DNA Polymerase II was shown by the value obtained by the method for determination of an enzyme activity described in Example 1. In addition, unless specified otherwise, the reaction solution comprising a commercially available enzyme was prepared in accordance with the instruction for each enzyme, or prepared by using a reaction buffer attached thereto. Unless specified otherwise, PCR was carried out by using GeneAmp PCR System 9600 (manufactured by Perkin-Elmer).

EXAMPLE 1

Preparation of Pfu DNA Polymerase II

Pfu DNA Polymerase II was purified from bacterial cells obtained by culturing *Escherichia coli* JM109/pFU1001 (FERM BP-5579), which was *Escherichia coli* JM109 transformed with plasmid pFU1001 carrying a gene encoding Pfu DNA Polymerase II, and used in the following procedures. Here, the culture of the transformant and the purification of the enzyme were carried out in accordance with the method described in WO97/24444 (for instance, pages 28-29, Example 3, and the like).

Incidentally, the enzyme activity of Pfu DNA Polymerase II was determined in the following manner. An activated calf thymus DNA (manufactured by Worthington) (activated DNA) was used as a substrate. DNA activation and determination of DNA polymerase activity were carried out by the method described in *DNA Polymerase from Escherichia coli*, 263-276 (authored by C. C. Richardson), published by Harper & Row, edited by D. R. Davis. To 5 µl of a sample of which the activity was to be determined was added 45 µl of a reaction mixture [20 mM Tris-hydrochloric acid (pH 9.0), 15 mM magnesium chloride, 2 mM 2-mercaptoethanol, 0.2 mg/ml activated DNA, 40 µM each of dATP, dCTP, dGTP and dTTP, 60 mM [$^3$H]-dTTP (manufactured by Amersham)]. The resulting mixture was reacted at 75° C. for 5 minutes. A 40 µl portion of this reaction mixture was then spotted onto DE paper (manufactured by Whatman) and washed with 5% by weight $Na_2HPO_4$ five times. Thereafter, the remaining radioactivity on the DE paper was determined using a liquid scintillation counter. The amount of enzyme which incorporated 10 nmol of [$^3$H]-dTMP per 30 minutes into the substrate DNA, determined by the above-described enzyme activity determination method, was defined as 1 U of the enzyme.

EXAMPLE 2

Preparation of Primers

Eleven kinds of primers λ1 to λ5, λ7 to λ10 and λL36 and λR485 were synthesized on the basis of the nucleotide sequences of λDNA. The nucleotide sequences for the primers λ1 to λ5 and λ8 to λ10 are respectively shown in SEQ ID NOs: 3 to 10 of Sequence Listing. In addition, the nucleotide sequence for λ7 is shown in SEQ ID NO: 11 of Sequence Listing. Further, the nucleotide sequences for λL36 and λR485 are respectively shown in SEQ ID NOs: 12 to 13 of Sequence Listing. The chain lengths of amplified DNA fragments are shown in Table 1, the fragments being amplified by PCR with λDNA as a template using the combinations of these primers. Further, 3 kinds of primers Eco1, Eco2 and Eco5 were synthesized on the basis of the nucleotide sequence of *Escherichia coli* genomic DNA. The nucleotide sequences of Eco1, Eco2 and Eco5 are respectively shown in SEQ ID NOs: 14 to 16 of Sequence Listing. The chain lengths of amplified DNA fragments are shown in Table 1, the fragments being amplified by PCR with *E. coli* genomic DNA as a template using the combinations of these primers. Further, 2 kinds of primers ApoE-1 and ApoE-2 were synthesized on the basis of the nucleotide sequence of human ApoE region. The nucleotide sequences of ApoE-1 and ApoE-2 are respectively shown in SEQ ID NOs: 17 to 18 of Sequence Listing. The chain lengths of amplified DNA fragments are shown in Table 1, the fragments being amplified by PCR with human genomic DNA as a template using the combinations of these primers.

TABLE 1

| Primer Pair | Chain Length of Amplified DNA Fragment (kb) |
|---|---|
| λ1/λ2 | 0.5 |
| λ1/λ3 | 1 |
| λ1/λ4 | 2 |
| λ1/λ5 | 4 |
| λ1/λ7 | 8 |
| λ1/λ8 | 10 |
| λ1/λ9 | 12 |
| λ1/λ10 | 15 |
| λL36/λR485 | 48.5 |
| Eco1/Eco2 | 2 |
| Eco1/Eco5 | 10 |
| ApoE-1/ApoE-2 | 0.44 |

EXAMPLE 3

Enhancement of DNA Synthesis Reaction by Acidic Substance (1) Effects on Activity of Pfu DNA Polymerase II The sulfated-fucose-containing polysaccharide-F obtained by the method described in WO97/26896 (for instance, Example 7, page 77, line 8 to page 78, line 13; Example 9, page 79, lines 7 to 18, and the like), the calf thymus DNA (manufactured by Worthington), heparin (manufactured by Wako Pure Chemicals) were used as acidic substances to examine the effects of these acidic substances imparted on the activity of Pfu DNA Polymerase II.

A reaction mixture comprising λDNA as a template, primers λ1 and λ3 as a primer pair, and Pfu DNA Polymerase II as DNA polymerase was prepared, and PCR was carried out. The composition of the reaction mixture is as follows.
Composition of Reaction Mixture:
10 mM Tris-hydrochloric acid (pH 9.2), 75 mM potassium chloride, 6 mM magnesium chloride, 0.4 mM each of dATP, dCTP, dGTP and dTTP, 0.01% BSA, 1.25 U of Pfu DNA Polymerase II, 500 pg of λDNA, and 5 pmol each of primers λ1 and λ3 (a final volume being 25 µl).

Further, 5 ng of the sulfated-fucose-containing polysaccharide-F, 200 ng of the calf thymus DNA, or 0.5 ng, 1 ng, 2 ng or 5 ng of heparin was respectively added to the above reaction mixture.

The reaction was carried out in 25 cycles, wherein one cycle of reaction comprises a process consisting of 98° C., 0 seconds—68° C., 0 seconds. Here, in the present specification, the description such as "98° C., 0 seconds," "68° C., 0 seconds" shows that the reactor is programmed so that the shift to the next temperature setting takes place simultaneously as the temperature reaches the set temperature.

After the termination of reaction, 5 µl of the resulting reaction mixture was subjected to electrophoresis on 1% agarose gel containing ethidium bromide in an amount of 0.00005%. The gel after electrophoresis was subjected to ultraviolet irradiation, to visualize a band ascribed to the amplified fragment, whereby an amplified fragment was confirmed. As a result, there was confirmed that an expected fragment of 1 kb was excellently amplified in any case where the acidic substances were added. When 0.5 ng of heparin was added, the fragment was especially highly efficiently amplified. On the other hand, for a similar reaction mixture except that an acidic substance was not added, when PCR was carried out under the above conditions, an amplified fragment of 1 kb could not be confirmed.

Further, the studies on the amplification of long chain length of DNA were carried out. A similar reaction mixture for PCR as above except that the amount of λDNA as a template was changed to 2.5 ng, and that the primer pair was changed to primers λ1 and λ5 or primers λ1 and λ10, respectively, was prepared. Here, 200 ng of the calf thymus DNA or 5 ng of the sulfated-fucose-containing polysaccharide-F was added as an acidic substance. The reaction was carried out in 30 cycles, wherein one cycle of reaction comprises a process consisting of 98° C., 0 seconds—68° C., 5 minutes. As a result, when the calf thymus DNA or the sulfated-fucose-containing polysaccharide-F was added, an amplified fragment of 4 kb was confirmed for the primers λ1 and λ5, and an amplified fragment of 15 kb was confirmed for primers λ1 and λ10, respectively. On the other hand, in a case where these acidic substances were not added, amplified fragments could not be confirmed with either of the primer pairs.

(2) Effects of Pfu DNA Polymerase I on DNA Synthesis Reaction

The effects of the sulfated-fucose-containing polysaccharide-F, which is an acidic substance, imparted on the activity of Pfu DNA Polymerase I were examined. Here, an enzyme prepared by utilizing recombinant DNA technique (Cloned Pfu DNA Polymerase, manufactured by Stratagene) was used for Pfu DNA Polymerase I.

A reaction mixture comprising λDNA as a template, primers λ1 and λ2 as a primer pair, and Pfu DNA Polymerase I as DNA polymerase was prepared, and PCR was carried out. The composition of the reaction mixture is as follows.
Composition of Reaction Mixture:
Pfu DNA Polymerase I buffer (manufactured by Stratagene), 0.2 mM each of dATP, dCTP, dGTP and dTTP, 1.25 U of Pfu DNA Polymerase I, 500 pg of template DNA, and 5 pmol each of primers λ1 and λ2 (a final volume being 25 µl). Two kinds of reaction mixtures were prepared: One with the addition of 20 ng of the sulfated-fucose-containing polysaccharide-F to the reaction mixture, and one without addition.

The reaction in 25 cycles was carried out for the prepared reaction mixture, wherein one cycle of reaction comprises a process consisting of 94° C., 30 seconds—55° C., 30 seconds—72° C., 60 seconds. Thereafter, 5 µl of the resulting reaction mixture was subjected to electrophoresis on 1% agarose gel, whereby an amplified DNA fragment was confirmed. The amount of the amplified DNA fragment of 0.5 kb was visualized in the same manner as described above, and compared. As a result, it was found that the amount of DNA amplified in the reaction mixture added with sulfated-fucose-containing polysaccharide-F was larger. From this finding, it was confirmed that the DNA amplification efficiency by Pfu DNA Polymerase I is improved by the addition of the sulfated-fucose-containing polysaccharide-F.

EXAMPLE 4

PCR Using Two Kinds of DNA Polymerases Each Having 3'→5' Exonuclease Activity

Studies were made on PCR simultaneously using both Pfu DNA Polymerase II and Pfu DNA Polymerase I, each of which is DNA polymerase having 3'→5' exonuclease activity. Here, Cloned Pfu DNA Polymerase (manufactured by Stratagene) mentioned above was used for Pfu DNA Polymerase I.
(1) PCR Using Mixture of Pfu DNA Polymerase I and Pfu DNA Polymerase II A reaction mixture comprising λDNA as a template, and primers λ1 and λ8 as a primer pair, was prepared, and PCR was carried out. In this PCR, both Pfu DNA Polymerase I and Pfu DNA Polymerase II were used. The composition of the reaction mixture is as follows.
Composition of Reaction Mixture:
10 mM Tris-hydrochloric acid (pH 9.2), 75 mM potassium chloride, 6 mM magnesium chloride, 0.4 mM each of dATP, dCTP, dGTP and dTTP, 0.01% BSA, 500 pg of template DNA, and 5 pmol each of primers λ1 and λ8

To the reaction mixture were added 0.375 U of Pfu DNA Polymerase II, and 0.125, 0.375, 0.75 or 1.25 U of Pfu DNA Polymerase I, respectively, to make up a final volume of the reaction mixture of 25 µl. In addition, as controls, a reaction mixture prepared by adding only Pfu DNA Polymerase I, and a reaction mixture prepared by adding only Pfu DNA Polymerase II were also prepared.

The reaction in 25 cycles was carried out for each of these reaction mixtures, wherein one cycle of reaction comprises a process consisting of 98° C., 0 seconds—68° C., 3 minutes. Thereafter, 5 µl of the resulting reaction mixture was subjected to electrophoresis on 1% agarose gel containing ethidium bromide in an amount of 0.00005%, whereby an amplified fragment was confirmed. As a result, amplification of a DNA fragment of 10 kb could not be confirmed by the addition of Pfu DNA Polymerase I alone regardless of the amount thereof. In addition, while a very slight amount of a fragment of 10 kb could be found by the addition of Pfu DNA Polymerase II alone, it was confirmed that amplification efficiency of a fragment of 10 kb was improved in an amount-dependent manner by adding Pfu DNA Polymerase I to Pfu DNA Polymerase II.
(2) Amplification of DNA Fragments Having Different Chain Lengths Using λDNA as a template, and each of primers λ1 and λ3, primers λ1 and λ4, or primers λ1 and λ5 as a primer pair, the reaction mixture having the following composition was prepared.
Composition of Reaction Mixture: 10 mM Tris-hydrochloric acid (pH 9.2), 75 mM potassium chloride, 6 mM magnesium chloride, 0.4 mM each of dATP, dCTP, dGTP and dTTP, 0.01% BSA, 1.25 U of Pfu DNA Polymerase I and 1.25 U of Pfu DNA Polymerase II, 500 pg of λDNA, and 5 pmol each of the primers, 5 ng or 50 ng of sulfated-fucose-containing polysaccharide-F (a final volume being 25 µl). In addition, as a control, one without addition of sulfated-fucose-containing polysaccharide-F was prepared.

The reaction in 30 cycles was carried out for each of these reaction mixtures, wherein one cycle of reaction comprises a process consisting of 98° C., 0 seconds—68° C., 0 seconds. Thereafter, 5 µl of the resulting reaction mixture was subjected to electrophoresis on 1% agarose gel containing ethidium bromide in an amount of 0.00005%, whereby an amplified fragment was confirmed. As a result, amplification of a DNA fragment of 1 kb, 2 kb or 4 kb could be confirmed, depending upon the primer pair used. Regarding sulfated-fucose-containing polysaccharide-F, one added in an amount of 50 ng showed more excellent amplification efficiency as compared to the one added in an amount of 5 ng. On the other hand, in a case of one without addition, amplified fragments could not be confirmed.

EXAMPLE 5

Comparison with Conventional PCR Techniques (1) Amplification of Long Chain DNA

As to the amplification reaction of a DNA fragment of 10 to 15 kb using λDNA as a template, a comparison was made between the reaction system described in item (2) of Example 4 and that for LA-PCR method using a combination of DNA polymerase having 3'→5' exonuclease activity and DNA polymerase having no such activity. Here, the reaction mixture for LA-PCR was prepared by using TaKaRa LA PCR Kit Ver. 2 (manufactured by Takara Shuzo Co., Ltd.).

Using each of primers λ1 and λ8, primers λ1 and λ9, or primers λ1 and λ10 as a primer pair, the reaction mixture having the following composition was prepared.
Composition of Reaction Mixture:
10 mM Tris-hydrochloric acid (pH 9.2), 75 mM potassium chloride, 6 mM magnesium chloride, 0.4 mM each of dATP, dCTP, dGTP and dTTP, 0.01% BSA, 1.25 U of Pfu DNA Polymerase I and 1.25 U of Pfu DNA Polymerase II, 500 pg of λDNA, and 5 pmol each of the primers, 50 ng of sulfated-fucose-containing polysaccharide-F (a final volume being 25 µl).

In addition, a reaction mixture for LA-PCR (a final volume being 25 µl) has the same amounts of template DNA and primers as the above-mentioned reaction mixture was prepared by using TaKaRa LA PCR Kit Ver. 2 mentioned above.

The reaction in 25 cycles was carried out for each of these reaction mixtures, wherein one cycle of reaction comprises a process consisting of 98° C., 0 seconds—68° C., 3 minutes. Thereafter, 5 µl of the resulting reaction mixture was subjected to electrophoresis on 1% agarose gel containing ethidium bromide in an amount of 0.00005%, whereby an amplified fragment was confirmed. As a result, when Pfu DNA Polymerase I and Pfu DNA Polymerase II described in item (2) of Example 5 were used in combination, amplification of a DNA fragment of each of 10 kb, 12 kb and 15 kb for each primer pair was confirmed.

On the other hand, in the reaction employing the conventional LA-PCR, while amplification of a fragment of 10 kb was confirmed, amplification of fragments of 12 kb and 15 kb could not be found.

Incidentally, when amplification of the fragment of 12 kb was tried by changing the conditions for one cycle to one comprising a process consisting of 98° C., 0 seconds—68° C., 5 minutes, amplification was found also for the reaction mixture for LA-PCR in this case.
(2) Amplification by Short Time Reaction of Short Chain DNA As to the amplification reaction of a DNA fragment of 0.5 to 4 kb using λDNA as a template, a comparison was made between the reaction system described in item (2) of Example 4 and that for LA-PCR method or that for KOD DNA Polymerase, which has been known to have high DNA synthesizing rate. Here, the reaction mixture for LA-PCR was prepared by using TaKaRa LA PCR Kit Ver. 2, and the reaction mixture for KOD DNA Polymerase was prepared by using KOD DNA Polymerase, manufactured by TOYOBO CO., LTD. and attached reaction buffer, respectively.

Using each of primers λ1 and λ2, primers λ1 and λ3, or primers λ1 and λ5 as a primer pair, the reaction mixture having the following composition was prepared.
Composition of Reaction Mixture:
10 mM Tris-hydrochloric acid (pH 9.2), 75 mM potassium chloride, 6 mM magnesium chloride, 0.4 mM each of dATP, dCTP, dGTP and dTTP, 0.01% BSA, 1.25 U of Pfu DNA Polymerase I and 1.25 U of Pfu DNA Polymerase II, 500 pg of λDNA, and 5 pmol each of the primers, 50 ng of sulfated-fucose-containing polysaccharide-F (a final volume being 25 µl).

In addition, using the same primer pair as the above-mentioned reaction mixture, a reaction mixture for LA-PCR and a reaction mixture for KOD DNA Polymerase (a final volume being both 25 µl) were prepared. Here, to these two kinds of the reaction mixtures, template λDNA was added 2500 pg each.

The reaction in 25 cycles was carried out for each of these reaction mixtures, wherein one cycle of reaction comprises a process consisting of 98° C., 0 seconds—68° C., 0 seconds. Thereafter, 5 µl of the resulting reaction mixture was subjected to electrophoresis on 1% agarose gel containing ethidium bromide in an amount of 0.00005%, whereby an amplified fragment was confirmed. As a result, when Pfu DNA Polymerase I and Pfu DNA Polymerase II described in item (2) of Example 5 were used in combination, amplification of a DNA fragment of each of 0.5 kb, 1 kb and 4 kb for each primer pair was confirmed.

On the other hand, in the conventional reaction mixture for LA-PCR or reaction mixture for KOD DNA Polymerase, only slight amplification of a DNA fragment of 0.5 kb could be found, even though the reaction mixtures contained template DNA in a five-fold amount.

(3) Comparison of DNA Detection Sensitivity

As to the amplification reaction of a DNA fragment using a slight amount of λDNA as a template, a comparison was made between the reaction system described in item (2) of Example 4 and that for LA-PCR method. Here, the reaction mixture for LA-PCR was prepared by using TaKaRa LA PCR Kit Ver. 2.

Using primers λ1 and λ2 as a primer pair, the reaction mixture having the following composition was prepared.
Composition of Reaction Mixture:
10 mM Tris-hydrochloric acid (pH 9.2), 75 mM potassium chloride, 6 mM magnesium chloride, 0.4 mM each of dATP, dCTP, dGTP and dTTP, 0.01% BSA, 1.25 U of Pfu DNA Polymerase I and 1.25 U of Pfu DNA Polymerase II, 0.05 fg of λDNA, and 5 pmol each of the primers, and 50 ng of sulfated-fucose-containing polysaccharide-F (a final volume being 25 µl).

In addition, a reaction mixture for LA-PCR having the same amounts of template DNA and primers as the above-mentioned reaction mixture was prepared.

The reaction in 50 cycles was carried out for each of these reaction mixtures, wherein one cycle of reaction comprises a process consisting of 98° C., 0 seconds—68° C., 0 seconds. Thereafter, 5 µl of the resulting reaction mixture was subjected to electrophoresis on 1% agarose gel containing ethidium bromide in an amount of 0.00005%, whereby an amplified fragment was confirmed. As a result, amplification of a DNA fragment of 0.5 kb could be confirmed only in the reaction system described in item (2) of Example 4.

Next, the primer pairs were changed to primers λ1 and λ8, and the two kinds of reaction mixtures in the same manner as mentioned above were similarly prepared. The reaction in 50 cycles was carried out for each of these reaction mixtures, wherein one cycle of reaction comprises a process consisting of 98° C., 0 seconds—68° C., 3 minutes. Thereafter, 5 µl of the resulting reaction mixture was subjected to electrophoresis on 1% agarose gel containing ethidium bromide in an amount of 0.00005%, whereby an amplified fragment was confirmed. As a result, amplification of a DNA fragment of 10 kb could be found in the reaction system described in item (2) of Example 4, whereas no amplification of a DNA fragment was found in the conventional reaction mixture for LA-PCR.

EXAMPLE 6

Preparation of Sulfated-Fucose-Containing Polysaccharide-F by Extraction with Hot Water The sulfated-fucose-containing polysaccharide-F used in the subsequent examples was purified by the following process. A preparation example of sulfated-fucose-containing polysaccharide-F is given hereinbelow.

Gagome kombu was sufficiently dried, and thereafter 20 kg, a weight on a dry basis, of the Gagome kombu was pulverized. Next, the resulting dry powder was suspended in 900 liters of tap water containing 7.3 kg of calcium chloride•dihydrate, and the temperature was raised to 90° C. over a period of 40 minutes with stirring. The extraction was carried out for one hour with keeping at 90° to 95° C. Thereafter, the resulting solution was cooled to 20° C., stopped stirring, and allowed to stand overnight, to give an extract.

Next, solid-liquid separation was carried out using a centrifuge (Model CNA, manufactured by Westfalia Separator Inc.). About 900 liters of supernatant of the solid-liquid separation was obtained from the above extract by using the centrifuge. Three-hundred and sixty liters of the supernatant was filtered with a SPARKLER FILTER (manufactured by Nippon Senshoku Kikai) incorporated with a filter of a size of 3 µm (manufactured by Nippon Shokuhin Rozai). The filtrate was concentrated to a volume of 20 liters by UF membrane ("FE10-FC-FUS0382," manufactured by DAICEL CHEMICAL INDUSTRIES, LTD.) having a fractionated molecular weight of 30000. Thereafter, 20 liters of tap water was added to the resulting concentrate, and the dilution was concentrated again to a volume of 20 liters. The dilution-concentration operations as described above were repeated five time, to give 25 liters of a concentrate.

To 700 ml of the above concentrate were added 0.2 M calcium chloride and 20 mM sodium acetate as a final concentration. Thereafter, the resulting mixture was dialyzed against 20 mM sodium acetate-equilibrated buffer (pH 6.0) containing 0.2 M calcium chloride. The solution after the dialysis treatment was applied to 3500 ml of DEAE-Sepharose FF column (column inner diameter: 9.7 cm) equilibrated with 10 liters of the above equilibrated buffer, and washed with 5 liters of the equilibrated buffer. The elution was carried out under 3-step gradient conditions given hereinbelow.

Incidentally, the flow rate of the chromatography was set at 3500 ml/1 hour. Gradient Conditions:
1] linear gradient of 0 to 0.5 M sodium chloride (amount of eluent: 4.5 liters)
2] linear gradient of 0.5 to 1.0 M sodium chloride (amount of eluent: 4.5 liters)
3] linear gradient of 1.0 to 2.0 M sodium chloride (amount of eluent: 4.5 liters)

The eluent was collected 250 ml per one fraction. Each fraction was subjected to sugar quantification by phenol sulfuric acid method, and to uronic acid quantification by carbazole-sulfuric acid method. As a result, fractions of Fraction Nos. 40 to 53, which were fractions having high sugar contents and low contents of uronic acid, were obtained. The fractions of Fraction Nos. 40 to 53 are referred to "sulfated-fucose-containing polysaccharide-F fractions." Each of the sulfated-fucose-containing polysaccharide-F fractions was concentrated with a ultrafiltration membrane of 100000, and thereafter the concentrate was dialyzed against 50 mM sodium citrate, and further dialyzed overnight against distilled water. Subsequently, the mixture was lyophilized, to give 1.696 g of sulfated-fucose-containing polysaccharide-F from the sulfated-fucose-containing polysaccharide-F fraction.

EXAMPLE 7

Preparation of Sulfated-Fucose-Containing Polysaccharide-U by Extraction with Hot Water The sulfated-fucose-containing polysaccharide-U used in the subsequent examples was purified by the following process. A preparation example of sulfated-fucose-containing polysaccharide-U is given hereinbelow.

Two tons of Gagome seaweed was pulverized, and the resulting dry powder was suspended in 44 kl of tap water containing 730 kg of calcium chloride•dihydrate, and the temperature was raised to 95° C. over a period of 1 hour and 35 minutes with stirring. The extraction was carried out for 2 hours with keeping at 95° C. Thereafter, the resulting solution was cooled overnight to room temperature.

Next, solid-liquid separation was carried out by using a decanter (manufactured by Tanabe Wiltech). The operating conditions were such that the separation was carried out at 3000 to 3300 rpm (2560 G) over a period of about 8 hours. The resulting supernatant of the solid-liquid separation was concentrated to a volume of 5 liters with a UF membrane ("FE10-FC-FUS0382," manufactured by DAICEL CHEMICAL INDUSTRIES, LTD.) having a fractionated molecular weight of 30000. Thereafter, the concentrate was subjected to UF desalting.

The above desalted solution was subjected to turbid removal with LINT FILTER (manufactured by Naigai Joki) incorporated with ADVANTEC #327 filter paper (manufactured by ADVANTEC). The filtrate was sterilized at 98° C. for 40 seconds with a plate heater (manufactured by Hisaka Seisakusho). The resulting extract was about 4620 liters. A part of the extract was lyophilized with a lyophilizer (manufactured by Kyowa Shinku Gijutsu).

Three-hundred and forty grams of the lyophilized product was dissolved in 21.2 liters of 20 mM sodium acetate-equilibrated buffer (pH 6.0) containing 0.2 M calcium chloride. The solution was applied to about 35 liters of DEAE-Sepharose FF column (column inner diameter: 35 cm) equilibrated with the above equilibrated buffer, and washed with 70 liters of the equilibrated buffer. The elution was carried out under 3-step gradient conditions given hereinbelow.

Incidentally, the flow rate of the chromatography was set at 35 liters/1 hour. Gradient Conditions:

1] linear gradient of 0 to 0.5 M sodium chloride (amount of eluent: 120 liters)
2] linear gradient of 0.5 to 1.0 M sodium chloride (amount of eluent: 120 liters)
3] linear gradient of 1.0 to 1.5 M sodium chloride (amount of eluent: 120 liters)

The eluent was collected 10 liters per one fraction. Each fraction was subjected to sugar quantification by phenol sulfuric acid method, and to uronic acid quantification by carbazole-sulfuric acid method. As a result, fractions of Fraction Nos. 4 to 16, which were fractions having high sugar contents and high contents of uronic acid were obtained. The fractions of Fraction Nos. 4 to 16 are referred to "sulfated-fucose-containing polysaccharide-U fractions." Each of the sulfated-fucose-containing polysaccharide-U fractions was concentrated with a ultrafiltration membrane having a cut-off molecular weight of 10000. Thereafter, the resulting concentrate was dialyzed by using a cellulose tube having a cut-off molecular weight of 12000 to 14000. First, the dialysis was carried out by twice an operation of exchanging an aqueous solution of 50 mM trisodium citrate•dihydrate every 3 to 4 hours with the aqueous solution, and thereafter overnight against the aqueous solution. Next, the dialysis was carried out by twice an operation of exchanging distilled water every 3 to 4 hours with distilled water, and thereafter overnight against distilled water. Subsequently, the mixture was lyophilized, to give 37.6 g of sulfated-fucose-containing polysaccharide-U from the sulfated-fucose-containing polysaccharide-U fraction.

EXAMPLE 8

Enhancement of DNA Synthesis Reaction of Pfu DNA Polymerase II by Acidic Substances In the following example, PCR was carried out in Fast mode by using TaKaRa PCR Thermal Cycler Personal (manufactured by Takara Shuzo Co., Ltd.).

(1) Effects of Sulfated-fucose-containing Polysaccharide-F, Dextran Sulfate Powder and Sodium Alginate on Activity of Pfu DNA Polymerase II Using the sulfated-fucose-containing Polysaccharide-F obtained in Example 6 described above, dextran sulfate powder (manufactured by Onco), or sodium alginate (100 to 150 centipoises, manufactured by Wako Pure Chemicals), the effects of these acidic substances on the activity of Pfu DNA Polymerase II were examined. A reaction mixture comprising λDNA as a template, primers λ1 and λ2 as a primer pair, and Pfu DNA Polymerase II as DNA polymerase was prepared, and PCR was carried out. The composition of the reaction mixture is as follows.

Composition of Reaction Mixture:

10 mM Tris-hydrochloric acid, pH 9.2, 75 mM potassium chloride, 6 mM magnesium chloride, 0.4 mM each of dATP, dCTP, dGTP and dTTP, 0.01% BSA, 1.25 U of Pfu DNA Polymerase II, 100 pg of λDNA, and 5 pmol each of primers λ1 and λ2 (a final volume being 25 µl). Further, 10 ng of the sulfated-fucose-containing polysaccharide-F, 10 ng of dextran sulfate powder, or 1 µg of sodium alginate was respectively added to the above reaction mixture.

The reaction in 25 cycles was carried out for each of these reaction mixtures, wherein one cycle of reaction comprises a process consisting of 98° C., 5 seconds—66° C., 15 seconds. Thereafter, 5 µl of the resulting reaction mixture was subjected to electrophoresis on 1% agarose gel containing ethidium bromide in an amount of 0.00005%, whereby an amplified fragment was confirmed. The results are shown in Table 2.

TABLE 2

| Acidic Substance | Amount Added | Amplification Results |
|---|---|---|
| Sulfated-fucose-containing Polysaccharide-F | 10 ng | ++ |
| Dextran Sulfate Powder | 10 ng | + |
| Sodium Alginate | 1 µg | + |
| No Addition | | − |

++: Intensive amplification being observed;
+: Amplification being observed;
±: Slight amplification being observed; and
−: No amplification being observed.

As shown in Table 2, there was confirmed that an expected fragment of 0.5 kb was excellently amplified in any case where acidic substances were added. On the other hand, for a similar reaction mixture without addition of the acidic substances, when PCR was carried out under the above conditions, an amplified fragment of 0.5 kb could not be confirmed.

(2) Effects of Sulfated-Fucose-Containing Polysaccharide-F, Sulfated-Fucose-Containing Polysaccharide-U and Sodium Polyglutamate on DNA Synthesis Reaction by Pfu DNA Polymerase II Further, studies were conducted on the effects of the sulfated-fucose-containing polysaccharide-F obtained in Example 6 described above, the sulfated-fucose-containing polysaccharide-U obtained in Example 7 described above, or sodium polyglutamate (manufactured by Sigma) as an acidic substance. A reaction mixture for PCR was prepared in the same manner as described above except for changing the amount of template λDNA to 500 pg and the primer pairs to primers λ1 and λ3. Five nanograms of the sulfated-fucose-containing polysaccharide-F, 5 ng, 10 ng, 20 ng or 30 ng each of the sulfated-fucose-containing polysaccharide-U, or 250 ng, 500 ng, 750 ng or 1000 ng each of sodium polyglutamate was respectively added to the above reaction mixture.

The reaction was carried out in 30 cycles, wherein one cycle of reaction comprises a process consisting of 98° C., 5 seconds—66° C., 15 seconds. After the termination of the reaction, 5 µl of the resulting reaction mixture was subjected to electrophoresis on 1% agarose gel containing ethidium bromide in an amount of 0.00005%, whereby an amplified fragment was confirmed. The results are shown in Table 3.

TABLE 3

| Acidic Substance | Amount Added (ng) | Amplification Results |
|---|---|---|
| Sulfated-fucose-containing Polysaccharide-F | 5 | ++ |
| Sulfated-fucose-containing Polysaccharide-U | 5 | ++ |
| | 10 | + |
| | 20 | + |
| | 30 | ± |
| Sodium Polyglutamate | 250 | + |
| | 500 | + |
| | 750 | ++ |
| | 1000 | + |
| No Addition | | − |

++: Intensive amplification being observed;
+: Amplification being observed;
±: Slight amplification being observed; and
−: No amplification being observed.

As shown in Table 3, when the sulfated-fucose-containing polysaccharide-F, the sulfated-fucose-containing polysaccharide-U, or sodium polyglutamate was added, an amplified fragment of 1 kb was confirmed in any of these cases. On the other hand, an amplified fragment of 1 kb could not be confirmed for one without addition of any of these acidic substances.

EXAMPLE 9

Enhancement of DNA Synthesis Reaction of Taq DNA Polymerase by Acidic Substances Using the sulfated-fucose-containing polysaccharide-F obtained in Example 6 described above or sodium alginate, the effects of these acidic substances imparted on TaKaRa Taq DNA Polymerase (manufactured by Takara Shuzo Co., Ltd.) were examined. In this example, PCR was carried out in normal mode by using TaKaRa PCR Thermal Cycler Personal.

A reaction mixture comprising λDNA as a template, primers λ1 and λ3 as a primer pair, and TaKaRa Taq DNA Polymerase as DNA polymerase was prepared, and PCR was carried out. The composition of the reaction mixture is as follows.

Composition of Reaction Mixture:
TaKaRa Taq DNA Polymerase buffer, 0.2 mM each of dATP, dCTP, dGTP and dTTP, 1.25 U of TaKaRa Taq DNA Polymerase, 100 pg of λDNA, and 10 pmol each of primers λ1 and λ3 (a final volume being 50 µl). Further, 0.1 ng or 0.25 ng each of the sulfated-fucose-containing polysaccharide-F or 1 µg of sodium alginate was respectively added to the above reaction mixture.

The reaction was carried out in 30 cycles, wherein one cycle of reaction comprises a process consisting of 98° C., 10 seconds—68° C., 1 minute. After the termination of the reaction, 5 µl of the resulting reaction mixture was subjected to electrophoresis on 1% agarose gel containing ethidium bromide in an amount of 0.00005%, whereby an amplified fragment was confirmed. The results are shown in Table 4.

TABLE 4

| Acidic Substance | Amount Added | Amplification Results |
|---|---|---|
| Sulfated-fucose-containing Polysaccharide-F | 0.1 ng | ++ |
| | 0.25 ng | ++ |
| Sodium Alginate | 1 µg | + |
| No Addition | | − |

++: Intensive amplification being observed;
+: Amplification being observed;
±: Slight amplification being observed; and
−: No amplification being observed.

As shown in Table 4, there was confirmed that an expected fragment of 1 kb was excellently amplified in any case where acidic substances were added. On the other hand, for a similar reaction mixture without addition of the acidic substances, when PCR was carried out under the above reaction conditions, an amplified fragment of 1 kb could not be confirmed.

EXAMPLE 10

Effects of Acidic Substances on DNA Polymerase for LA-PCR (1) The effects of the acidic substances were studied on LA-PCR method comprising a combination of DNA polymerase having 3'→5' exonuclease activity, and DNA polymerase having no such activity. A reaction mixture comprising λDNA as a template, primers λ1 and λ8 as a primer pair was prepared, and PCR was carried out. In this PCR, TaKaRa EX-Taq DNA Polymerase (manufactured by Takara Shuzo Co., Ltd.) was used. The composition of the reaction mixture is as follows.

In the following example, PCR was carried out in Fast mode by using TaKaRa PCR Thermal Cycler Personal (manufactured by Takara Shuzo Co., Ltd.).

Composition of Reaction Mixture:
a reaction mixture comprising TaKaRa EX-Taq DNA Polymerase buffer, 0.2 mM each of dATP, dCTP, dGTP and dTTP, 10 pg of λDNA, 1.25 U of TaKaRa EX-Taq DNA Polymerase, and 10 pmol each of primers λ1 and λ8 (a final volume being 50 μl). Further, 1 ng of the sulfated-fucose-containing polysaccharide-F or 0.5 μg of sodium alginate was respectively added to the above reaction mixture.

The reaction was carried out in 27 cycles, wherein one cycle of reaction comprises a process consisting of 98° C., 5 seconds—68° C., 3 minutes. After the termination of the reaction, 5 μl of the resulting reaction mixture was subjected to electrophoresis on 1% agarose gel containing ethidium bromide in an amount of 0.00005%, whereby an amplified fragment was confirmed. The results are shown in Table 5.

Further, PCR was carried out for a reaction having the same composition as the above reaction mixture except for using 100 pg of λDNA as template DNA, and adding 0.25 μg of sodium alginate or 1 ng of the sulfated-fucose-containing polysaccharide-F as an acidic substance.

The reaction was carried out in 29 cycles, wherein one cycle of reaction comprises a process consisting of 98° C., 5 seconds—68° C., 3 minutes. After the termination of the reaction, 5 μl of the resulting reaction mixture was subjected to electrophoresis on 1% agarose gel containing ethidium bromide in an amount of 0.00005%, whereby an amplified fragment was confirmed. The results are also shown in Table 5.

TABLE 5

| Amount of Template DNA | Acidic Substance | Amount Added | Amplification Results |
|---|---|---|---|
| 10 pg | Sulfated-fucose-containing Polysaccharide-F | 1 ng | ++ |
|  | Sodium Alginate | 0.5 μg | ++ |
|  | No Addition | — | − |
| 100 pg | Sulfated-fucose-containing Polysaccharide-F | 1 ng | ++ |
|  | Sodium Alginate | 0.25 μg | ++ |
|  | No Addition | — | ± |

++: Intensive amplification being observed;
+: Amplification being observed;
±: Slight amplification being observed; and
−: No amplification being observed.

As shown in Table 5, there was confirmed that a fragment of 10 kb when adding an acidic substance was excellently amplified for any of the amounts of template DNA. On the other hand, when PCR was carried out under the above reaction conditions for a reaction mixture without addition of the acidic substances, an amplified fragment of 10 kb could be confirmed very slightly for the case where template DNA was 100 pg.

(2) The effects of the acidic substances were studied for KOD dash DNA Polymerase (manufactured by TOYOBO CO., LTD.), comprising a combination of DNA polymerase having 3'→5' exonuclease activity, and DNA polymerase having no such activity. A reaction mixture comprising λDNA as a template, primers λ1 and λ9 as a primer pair was prepared, and PCR was carried out. In the following example, PCR was carried out in Fast mode by using TaKaRa PCR Thermal Cycler Personal (manufactured by Takara Shuzo Co., Ltd.).

The composition of the reaction mixture is as follows.
Composition of Reaction Mixture:
exclusive buffer attached for KOD dash DNA Polymerase, 0.2 mM each of dATP, dCTP, dGTP and dTTP, 10 pg of λDNA, 2.5 U of KOD dash DNA Polymerase, and 10 pmol each of primers λ1 and λ9 (a final volume being 50 μl). Further, 1 ng of the sulfated-fucose-containing polysaccharide-F or 0.5 μg of sodium alginate was respectively added to the above reaction mixture.

The reaction was carried out in 25 cycles, wherein one cycle of reaction comprises a process consisting of 98° C., 5 seconds—68° C., 3 minutes. After the termination of the reaction, 5 μl of the resulting reaction mixture was subjected to electrophoresis on 1% agarose gel containing ethidium bromide in an amount of 0.00005%, whereby an amplified fragment was confirmed. The results are shown in Table 6.

TABLE 6

| Acidic Substance | Amount Added | Amplification Results |
|---|---|---|
| Sulfated-fucose-containing Polysaccharide-F | 1 ng | + |
| Sodium Alginate | 0.5 μg | ++ |
| No Addition |  | ± |

++: Intensive amplification being observed;
+: Amplification being observed;
±: Slight amplification being observed; and
−: No amplification being observed.

As shown in Table 6, there was confirmed that an expected fragment of 12 kb was excellently amplified in any case where acidic substances were added. On the other hand, for a similar reaction mixture without addition of the acidic substances, when PCR was carried out under the above reaction conditions, an amplified fragment of 12 kb could be only slightly confirmed.

EXAMPLE 11

PCR Using Two Kinds of DNA Polymerases Each Having 3'→5' Exonuclease Activity

Studies were conducted on PCR simultaneously using Pfu DNA Polymerase II and any one of KOD DNA Polymerase (manufactured by TOYOBO CO., LTD.), VENT DNA Polymerase (manufactured by New England Biolab), or DEEP VENT DNA Polymerase (manufactured by New England Biolab), each of which is DNA polymerase having 3'→5' exonuclease activity.

A reaction mixture comprising λDNA as a template, primers λ1 and λ8 as a primer pair was prepared, and PCR was carried out. In this PCR, a combination of Pfu DNA Polymerase II and KOD DNA Polymerase, a combination of Pfu DNA Polymerase II and VENT DNA Polymerase, or a combination of Pfu DNA Polymerase II and DEEP VENT DNA Polymerase was respectively used. The composition of the reaction mixture is as follows.
Composition of Reaction Mixture:
10 mM Tris-hydrochloric acid (pH 9.2), 75 mM potassium chloride, 6 mM magnesium chloride, 0.4 mM each of dATP, dCTP, dGTP and dTTP, 0.01% BSA, 500 pg of λDNA, and 5 pmol each of primers λ1 and λ8. To the above reaction mixture was respectively added 0.375 U of Pfu DNA Polymerase II, and 3.75 mU of KOD DNA Polymerase, 6.25 mU of VENT DNA Polymerase or DEEP VENT DNA Polymerase, the reaction mixture making up a final volume of 25 μl.

In addition, as controls, a reaction mixture in which Pfu DNA Polymerase II, KOD DNA Polymerase, VENT DNA Polymerase or DEEP VENT DNA Polymerase was added alone was prepared. The reaction in 30 cycles was carried out for each of these reaction mixtures, wherein one cycle of reaction comprises a process consisting of 98° C., 5 seconds—68° C., 3 minutes. Thereafter, 5 µl of the resulting reaction mixture was subjected to electrophoresis on 1% agarose gel containing ethidium bromide in an amount of 0.00005%, whereby an amplified DNA fragment was confirmed. The results are shown in Table 7.

TABLE 7

| Combination of DNA Polymerase (Polymerase A/Polymerase B) | Amount of Enzyme Used (Polymerase A/ Polymerase B) | Amplification Results |
|---|---|---|
| Pfu DNA Polymerase II/— | 0.375 U/— | ± |
| —/KOD DNA Polymerase | —/3.75 mU | − |
| —/VENT DNA Polymerase | —/6.25 mU | − |
| —/DEEP VENT DNA Polymerase | —/6.25 mU | − |
| Pfu DNA Polymerase II/ KOD DNA Polymerase | 0.375 U/3.75 mU | + |
| Pfu DNA Polymerase II/ VENT DNA Polymerase | 0.375 U/6.25 mU | + |
| Pfu DNA Polymerase II/ DEEP VENT DNA Polymerase | 0.375 U/6.25 mU | + |

++: Intensive amplification being observed;
+: Amplification being observed;
±: Slight amplification being observed; and
−: No amplification being observed.

As shown in Table 7, while an amplified fragment of 10 kb was not found when using KOD DNA Polymerase, VENT DNA Polymerase or DEEP VENT DNA Polymerase alone, there was found a slight amount of an amplified fragment of 10 kb when using Pfu DNA Polymerase II alone. Further, in a system where 0.375 U of Pfu DNA Polymerase II, and 3.75 mU of KOD DNA Polymerase, 6.25 mU of VENT DNA Polymerase or DEEP VENT DNA Polymerase is used in combination, there was confirmed that an amplification efficiency of a fragment of 10 kb was improved, as compared with the case of using Pfu DNA Polymerase II alone.

EXAMPLE 12

PCR was carried out by using in combination Pfu DNA Polymerase II obtained in Example 1 and Pfu DNA Polymerase I (manufactured by Stratagene), which is α-type DNA polymerase, and sodium alginate, which is an acidic substance.

A reaction mixture comprising λDNA as a template, primers λ1 and λ3 as a primer pair was prepared, and PCR was carried out. The composition of the reaction mixture is as follows.
Composition of Reaction Mixture:
reaction buffer for PCR (10 mM Tris-hydrochloric acid, pH 9.2, 75 mM potassium chloride, 6 mM magnesium chloride, 0.4 mM each of dATP, dCTP, dGTP and dTTP, 0.01% BSA, and 0.004% of sodium alginate), 10 pg of λDNA, and 5 pmol each of primers λ1 and λ3. To the above reaction mixture was added an enzyme solution containing 1.25 U of Pfu DNA Polymerase II and 1.14 U of Pfu DNA Polymerase I, the reaction mixture making up a final volume of 25 µl.

In addition, a reaction mixture without addition of sodium alginate was prepared as a control. The reaction in 30 cycles was carried out for each of these reaction mixtures, wherein one cycle of reaction comprises a process consisting of 98° C., 5 seconds—66° C., 15 seconds. Thereafter, 5 µl of the resulting reaction mixture was subjected to electrophoresis on 1% agarose gel containing ethidium bromide in an amount of 0.00005%, whereby an amplified DNA fragment was confirmed. The results are shown in Table 8.

TABLE 8

| Kinds of Kit Used | Amplification Results |
|---|---|
| Reaction Buffer (Containing 0.004% Sodium Alginate) | ++ |
| Reaction Buffer (Without Containing Sodium Alginate) | − |

++: Intensive amplification being observed;
+: Amplification being observed;
±: Slight amplification being observed; and
−: No amplification being observed.

As shown in Table 8, there was confirmed that amplification efficiency for a fragment of 1 kb was improved in the reaction in which Pfu DNA Polymerase I, Pfu DNA Polymerase II and sodium alginate were used in combination. Further, the above study has been conducted for commercially available sodium alginate for each viscosity (100 to 1000 centipoises), and as a result, completely the same improvements in the amplification efficiency for DNA synthesis were confirmed.

EXAMPLE 13

Preparation of Kit

A PCR kit (20 reactions) of the present invention was constructed by using Pfu DNA Polymerase II obtained in Example 1, Pfu DNA Polymerase I and sodium alginate, which is an acidic substance in combination.

The composition for the kit is shown below:

| | |
|---|---|
| 10 X Reaction Buffer for PCR<br>100 mM Tris-Hydrochloric Acid (pH 9.2)<br>750 mM Potassium Chloride<br>0.1% BSA<br>0.04% Sodium Alginate (100 to 150 centipoises) | 50 µl |
| 25 mM Magnesium Chloride Solution | 120 µl |
| 2.5 mM dNTP Mix (2.5 mM Each of dATP, dCTP, dGTP and dTTP) | 80 µl |
| Enzyme Mixed Solution for DNA Polymerases (2.5 U of Pfu DNA Polymerase II and 2.28 U of Pfu DNA Polymerase I/1 µl) | 10 µl |

A reaction mixture for PCR was prepared using the above kit. λDNA was used as a template. The composition for the reaction mixture is shown in Table 9.

TABLE 9

| Composition of Reaction Mixture | |
|---|---|
| 10 X PCR Reaction Buffer | 2.5 µl |
| Magnesium Chloride Solution | 6 µl |
| dNTP Mix | 4 µl |
| Enzyme Mixed Solution for DNA Polymerase | 0.5 µl |
| λDNA | 10 pg |
| λ1 Primer | 5 pmol |
| λ3 Primer | 5 pmol |
| Sterilized Distilled Water | Balance |
| Final Volume | 25 µl |

In addition, a reaction mixture having the same composition as described above except that sodium alginate was not contained was prepared as a control.

The reaction for the above reaction mixture was carried out under the PCR conditions shown in Example 12. As a result, there could be confirmed that the reaction mixture prepared by using the kit containing sodium alginate described above had improved amplification efficiency of a fragment of 1 kb, as compared to that of control.

EXAMPLE 14

Numerical Explanation on Enhancement of DNA Synthesis Reaction by Acidic Substance Using the sulfated-fucose-containing polysaccharide-F obtained in Example 6 described above, the effects on the activity of Pfu DNA Polymerase II were examined. A reaction mixture comprising λDNA as a template, primers λ1 and λ2 as a primer pair, and Pfu DNA Polymerase II as DNA polymerase was prepared, and PCR was carried out. The composition of the reaction mixture is as follows.
Composition of Reaction Mixture:
10 mM Tris-hydrochloric acid, pH 9.2, 75 mM potassium chloride, 6 mM magnesium chloride, 0.4 mM each of dATP, dCTP, dGTP and dTTP, 0.01% BSA, 1.25 U of Pfu DNA Polymerase II, 500 pg of λDNA, and 5 pmol each of primers λ1 and λ2 (a final volume being 25 µl). Further, 10 ng of the sulfated-fucose-containing polysaccharide-F was respectively added to the above reaction mixture.

The reaction in 30 cycles was carried out for each of these reaction mixtures, wherein one cycle of reaction comprises a process consisting of 98° C., 5 seconds—66° C., 15 seconds. Thereafter, 5 µl of the resulting reaction mixture was subjected to electrophoresis on 1% agarose gel containing ethidium bromide in an amount of 0.00005%, whereby an expected amplified fragment of 0.5 kb was confirmed. In addition, the agarose gel was analyzed by using a fluorescent image analyzer FM-BIO (manufactured by Takara Shuzo Co., Ltd.) to numerically explain the relative amount of the amplified fragment.

As a result, as compared with a case where a reaction system in which an acidic substance was not added was considered to be 1, one using sulfated-fucose-containing polysaccharide-F, which is an acidic substance, was 4.4. In other words, there could be confirmed that an amount of amplified product was multiplied by 4.4 by the addition of an acidic substance in PCR.

EXAMPLE 15

Enhancement of DNA Synthesis Reaction by Acidic Substance

Using a polyacrylic acid as an acidic substance, the effects on the activity of Pfu DNA Polymerase II were examined. A reaction mixture comprising λDNA as a template, primers λ1 and λ3 as a primer pair, and Pfu DNA Polymerase II as DNA polymerase was prepared, and PCR was carried out. The composition of the reaction mixture is as follows.
Composition of Reaction Mixture:
10 mM Tris-hydrochloric acid, pH 9.2, 75 mM potassium chloride, 6 mM magnesium chloride, 0.4 mM each of dATP, dCTP, dGTP and dTTP, 0.01% BSA, 1.25 U of Pfu DNA Polymerase II, 500 pg of λDNA, and 5 pmol each of primers λ1 and λ3 (a final volume being 25 µl). Further, 100 ng of a polyacrylic acid having an average molecular weight of about 5,000, about 25,000, about 250,000, or about 1,000,000 (each being manufactured by Wako Pure Chemicals) was respectively added to the above reaction mixture.

The reaction in 30 cycles was carried out for each of these reaction mixtures, wherein one cycle of reaction comprises a process consisting of 98° C., seconds—66° C., 15 seconds. Thereafter, 5 µl of the resulting reaction mixture was subjected to electrophoresis on 1% agarose gel containing ethidium bromide in an amount of 0.00005%, whereby an amplified fragment was confirmed. The results are shown in Table 10.

TABLE 10

| Acidic Substance | Average Molecular Weight | Amplification Results |
|---|---|---|
| Sodium Polyacrylate | 5,000 | ++ |
|  | 25,000 | ++ |
|  | 250,000 | ++ |
|  | 1,000,000 | ++ |
| No Addition |  | − |

++: Intensive amplification being observed;
+: Amplification being observed;
±: Slight amplification being observed; and
−: No amplification being observed.

As shown in Table 10, there was confirmed that an expected fragment of 1 kb was excellently amplified in any case where the sodium polyacrylate of any of the average molecular weights was added. On the other hand, for a similar reaction mixture without addition of the acidic substance, when PCR was carried out under the above reaction conditions, an amplified fragment of 1 kb could not be confirmed.

EXAMPLE 16

Effects of Acidic Substances on α-Type DNA Polymerase (1) Using sodium alginate, sodium hyaluronate (manufactured by Seikagaku Kogyo), or κ carrageenan (manufactured by Sigma), the effects of these acidic substances on α-type DNA polymerase were examined. A reaction mixture comprising λDNA as a template, primers λ1 and λ8 as a primer pair, and KOD DNA Polymerase (manufactured by TOYOBO CO., LTD.) as DNA polymerase was prepared, and PCR was carried out. The composition of the reaction mixture is as follows.
Composition of Reaction Mixture:
KOD DNA Polymerase Buffer I (manufactured by TOYOBO CO., LTD.) 0.2 mM each of dATP, dCTP, dGTP and dTTP, 0.625 U of KOD DNA Polymerase, 100 pg of λDNA, and 5 pmol each of primers λ1 and λ8 (a final volume being 25 µl). Further, 1 µg or 2.5 µg of sodium alginate, 0.1 µg or 0.5 µg of sodium hyaluronate, or 0.1 µg or 0.25 µg of κ carrageenan was respectively added to the above reaction mixture.

The reaction in 30 cycles was carried out for each of these reaction mixtures, wherein one cycle of reaction comprises a process consisting of 98° C., 5 seconds—68° C., 3 minutes. Thereafter, 5 µl of the resulting reaction mixture was subjected to electrophoresis on 1% agarose gel containing ethidium bromide in an amount of 0.00005%, whereby an amplified fragment was confirmed. The results are shown in Table 11.

TABLE 11

| Acidic Substance | Amount Added (μg) | Amplification Results |
|---|---|---|
| Sodium Alginate | 1 | ++ |
|  | 2.5 | ++ |
| Sodium Hyaluronate | 0.1 | + |
|  | 0.5 | + |
| κ Carrageenan | 0.1 | + |
|  | 0.25 | + |
| No Addition |  | ± |

++: Intensive amplification being observed;
+: Amplification being observed;
±: Slight amplification being observed; and
−: No amplification being observed.

As shown in Table 11, there was confirmed that an expected fragment of 10 kb was excellently amplified in any case where acidic substances were added. On the other hand, for a similar reaction mixture without addition of the acidic substances, when PCR was carried out under the above reaction conditions, an amplified fragment of 10 kb could be confirmed weakly.

(2) The effects on α-type DNA polymerase were also examined in the same manner as in item (1) above for sodium alginate, κ carrageenan, sodium heparan sulfate (manufactured by Sigma), sodium dermatan sulfate (manufactured by Sigma), potassium polyvinyl sulfate (manufactured by nacalaitesque) or sodium polystyrenesulfonate (two kinds: average molecular weights of 5,400 and 35,000, all manufactured by nacalaitesque). A reaction mixture comprising λDNA as a template, primers λ1 and λ8 as a primer pair, and KOD DNA Polymerase as DNA polymerase was prepared, and PCR was carried out. The composition of the reaction mixture is as follows.

Composition of Reaction Mixture:
KOD DNA Polymerase Buffer II (manufactured by TOYOBO CO., LTD.) 0.2 mM each of dATP, dCTP, dGTP and dTTP, 1.25 U of KOD DNA Polymerase, 100 pg of λDNA, and 10 pmol each of primers λ1 and λ8 (a final volume being 50 μl). Further, 2.5 μg or 5 μg of sodium alginate, 0.25 μg or 0.5 μg of κ carrageenan, or 125 ng, 250 ng or 375 ng of sodium dermatan sulfate, 500 ng of sodium heparan sulfate, 10 ng of potassium polyvinyl sulfate, 2.5 ng or 5 ng of sodium polystyrenesulfonate (average molecular weight: 5,400), or 5 ng of sodium polystyrenesulfonate (average molecular weight: 35,000) was respectively added to the above reaction mixture.

The reaction in 30 cycles was carried out for each of these reaction mixtures, wherein one cycle of reaction comprises a process consisting of 98° C., 5 seconds—68° C., 3 minutes. Thereafter, 5 μl of the resulting reaction mixture was subjected to electrophoresis on 1% agarose gel containing ethidium bromide in an amount of 0.00005%, whereby an amplified fragment was confirmed. The results are shown in Table 12.

TABLE 12

| Acidic Substance | Amount Added | Amplification Results |
|---|---|---|
| Sodium Alginate | 2.5 μg | ++ |
|  | 5 μg | ++ |
| κ Carrageenan | 0.25 μg | ++ |
|  | 0.5 μg | ++ |
| Sodium Dermatan Sulfate | 125 ng | + |
|  | 250 ng | + |
|  | 375 ng | + |

TABLE 12-continued

| Acidic Substance | Amount Added | Amplification Results |
|---|---|---|
| Sodium Heparan Sulfate | 500 ng | + |
| Potassium Polyvinyl Sulfate | 10 ng | + |
| Sodium Polystyrenesulfonate | 2.5 ng | + |
| (Average Molecular Weight: 5,400) | 5 ng | + |
| (Average Molecular Weight: 35,000) | 5 ng | + |
| No Addition |  | − |

++: Intensive amplification being observed;
+: Amplification being observed;
±: Slight amplification being observed; and
−: No amplification being observed.

As shown in Table 12, there was confirmed that an expected fragment of 10 kb was excellently amplified in any case where acidic substances were added. On the other hand, for a similar reaction mixture without addition of the acidic substances, when PCR was carried out under the above reaction conditions, an amplified fragment of 10 kb could not be confirmed.

EXAMPLE 17

Effects of Cationic Complexes on Various Kinds of DNA Polymerases

Using hexaamminecobalt (III) chloride ($[Co(NH_3)_6]Cl_3$) (manufactured by Sigma), tris(ethylenediamine)cobalt (III) chloride ($[Co(C_2H_8N_2)_3]Cl_3$) (manufactured by Aldrich), or tris(ethylenediamine)rhodium (III) trichloride•trihydrate ($[Rh(C_2H_8N_2)_3]Cl_3 \cdot 3H_2O$) (manufactured by Aldrich), the effects on the amplification reaction by various kinds of DNA polymerases were examined. As the DNA polymerases, TaKaRa Taq DNA Polymerase (hereinafter referred to as "Taq DNA Polymerase" manufactured by Takara Shuzo Co., Ltd.), Pyrobest DNA Polymerase (manufactured by Takara Shuzo Co., Ltd.) and ExTaq DNA Polymerase (manufactured by Takara Shuzo Co., Ltd.) were used.

A reaction mixture comprising Escherichia coli JM109 genomic DNA as a template, primers Eco1 and Eco2 as a primer pair, and DNA polymerase was prepared, and PCR was carried out. The compositions of the reaction mixture for each enzyme are as follows.

Compositions of Reaction Mixtures:
1) Reaction System for Taq DNA Polymerase
5 μl of buffer for 10×Taq PCR buffer (manufactured by Takara Shuzo Co., Ltd.), 0.2 mM each of dATP, dCTP, dGTP and dTTP, 1.25 U of Taq DNA Polymerase, 100 pg of Escherichia coli JM109 genomic DNA, and 10 pmol each of primers Eco1 and Eco2 (a final volume being 50 μl).
2) Reaction System for Pyrobest DNA Polymerase
5 μl of 10-fold concentrated Pyrobest buffer (manufactured by Takara Shuzo Co., Ltd.), 0.2 mM each of dATP, dCTP, dGTP and dTTP, 1.25 U of Pyrobest DNA Polymerase, 100 pg of Escherichia coli JM109 genomic DNA, and 10 pmol each of primers Eco1 and Eco2 (a final volume being 50 μl).
3) Reaction System for ExTaq DNA Polymerase
a reaction mixture comprising 5 μl of 10-fold concentrated buffer for TaKaRa ExTaq DNA Polymerase (manufactured by Takara Shuzo Co., Ltd.), 0.2 mM each of dATP, dCTP, dGTP and dTTP, 100 pg of Escherichia coli JM109 genomic DNA, 1.25 U of TaKaRa EX-Taq DNA Polymerase, and 10 pmol each of primers Eco1 and Eco2 (a final volume being 50 μl).

Further, an aqueous solution of the above-mentioned complexes each so as to have a final concentration of 50 μM, 100 μM, or 200 μM was added to the above reaction mixture.

The reaction was carried out in Fast mode by using TaKaRa PCR Thermal Cycler Personal (manufactured by Takara Shuzo Co., Ltd.). The reaction conditions are as follows. When using Taq DNA Polymerase and Pyrobest DNA Polymerase, the reaction in 30 cycles was carried out for each of these reaction mixtures, wherein one cycle of reaction comprises a process consisting of 98° C., 5 seconds—68° C., 2 minutes, and when using ExTaq DNA Polymerase, the reaction in 30 cycles was carried out for each of these reaction mixtures, wherein one cycle of reaction comprises a process consisting of 98° C., 5 seconds—68° C., 1 minute. After the termination of the reaction, 5 μl of the resulting reaction mixture was subjected to electrophoresis on 2% agarose gel containing ethidium bromide in an amount of 0.00005%. The gel after the electrophoresis was subjected to ultraviolet irradiation to visualize the band ascribed to the amplified product, whereby an amplified fragment was confirmed. The amount of amplified DNA was numerically explained by using a fluorescent image analyzer FM-BIO 100 (manufactured by Takara Shuzo Co., Ltd.). The results are shown in Table 13.

TABLE 13

| Cationic Complex | | DNA Polymerase | | |
| --- | --- | --- | --- | --- |
|  |  | Taq | Pyrobest | ExTaq |
| $[Co(NH_3)_6]Cl_3$ | 50 μM | 2.3 | 2.1 | 1.9 |
|  | 100 μM | 2.9 | 2.1 | 1.9 |
|  | 200 μM | — | 2.1 | — |
| $[Co(H_2NCH_2CH_2NH_2)_3]Cl_3$ | 50 μM | 2.6 | 2.1 | 2.0 |
|  | 100 μM | 3.0 | 2.2 | 2.0 |
|  | 200 μM | — | — | — |
| $[Rh(H_2NCH_2CH_2NH_2)_3]Cl_3$ | 50 μM | 1.4 | 1.4 | 1.3 |
|  | 100 μM | 2.1 | 1.7 | 1.5 |
|  | 200 μM | 2.5 | 2.0 | 1.7 |
| No Addition |  | 1 | 1 | 1 |

As a result, with regard to Taq DNA Polymerase, there was confirmed an increase in the amount of DNA amplified in about 1.4 times to about 3 times that of a case of no addition, in the reaction in which 50 μM or 100 μM of hexaamminecobalt (III) chloride, 50 μM or 100 μM of tris(ethylenediamine)cobalt (III) chloride, or 50 μM, 100 μM or 200 μM of tris(ethylenediamine)rhodium (III) trichloride was added.

Next, with regard to Pyrobest DNA Polymerase, there was confirmed an increase in the amount of DNA amplified in about 1.4 times to about 2.2 times that of a case of no addition, in the reaction in which 50 μM, 100 μM or 200 μM 5 of hexaamminecobalt (III) chloride, 50 μM or 100 μM of tris(ethylenediamine)cobalt (III) chloride, or 50 μM, 100 μM or 200 μM of tris(ethylenediamine)rhodium (III) trichloride was added.

Further, with regard to ExTaq DNA Polymerase, there was confirmed an increase in the amount of DNA amplified in about 1.3 times to about 2 times that of a case of no addition, in the reaction in which 50 μM or 100 μM of hexaamminecobalt (III) chloride, 50 μM or 100 μM of tris(ethylenediamine)cobalt (III) chloride, or 50 μM, 100 μM or 200 μM of tris(ethylenediamine)rhodium (III) trichloride was added.

EXAMPLE 18

Effects on Reaction Time by Addition of Hexaamminecobalt (III) Chloride

With regard to each DNA polymerase, the effects on shortening the reaction time by the addition of hexaamminecobalt (III) chloride were examined.

The DNA polymerases used and the composition for the reaction mixture were similar to those in Example 17, except for the cationic complex, where in cases of using Taq DNA Polymerase and Pyrobest DNA Polymerase, hexaamminecobalt (III) chloride was added so as to have a final concentration of 100 μM, and in a case of using ExTaq DNA Polymerase, hexaamminecobalt (III) chloride was added so as to have a final concentration of 50 μM, respectively.

The reaction was carried out in Fast mode by using TaKaRa PCR Thermal Cycler Personal. The reaction conditions are as follows. When using Taq DNA Polymerase and Pyrobest DNA Polymerase, the reaction in 30 cycles was carried out, wherein one cycle of reaction comprises a process consisting of 98° C., seconds—68° C., 60 seconds or 80 seconds or 100 seconds or 120 seconds. When using ExTaq DNA Polymerase, the reaction in 30 cycles was carried out, wherein one cycle of reaction comprises a process consisting of 98° C., 5 seconds—68° C., 30 seconds or 40 seconds or 50 seconds or 60 seconds.

On the other hand, as a control, the time period or number of cycles for annealing and extension reaction were determined so as to obtain the same amount of the amount of amplified product for one without addition of the cationic complex mentioned above.

After the termination of the reaction, 5 μL of the resulting reaction mixture was subjected to electrophoresis on 2% agarose gel containing ethidium bromide in an amount of 0.00005%. The gel after the electrophoresis was subjected to ultraviolet irradiation to visualize the band ascribed to the amplified product, whereby an amplified fragment was confirmed. The results are shown in Table 14.

TABLE 14

|  | Cationic Complex | |
| --- | --- | --- |
| DNA Polymerase | Addition | No Addition |
| Taq and Pyrobest | 98° C., 5 s - 68° C., 60 s<br>30 Cycles<br>(Time Period Required: 2953 s) | 98° C., 5 s - 68° C., 120 s<br>31 Cycles<br>(Time Period Required: 4911 s) |
| ExTaq | 98° C., 5 s - 68° C., 40 s<br>30 Cycles<br>(Time Period Required: 2294 s) | 98° C., 5 s - 60° C., 60 s<br>30 Cycles<br>(Time Period Required: 2953 s) |

As shown in Table 14, in the cases of using Taq DNA Polymerase and Pyrobest DNA polymerase, when hexaamminecobalt (III) chloride was added in an amount of 100 μM, the reaction time period could be shortened to about ⅗ that of the case of no addition. Further, in the case of using ExTaq DNA Polymerase, when hexaamminecobalt (III) chloride was added in an amount of 50 μM, the reaction time period could be shortened to about ⅘ that of the case of no addition.

EXAMPLE 19

Effects on Amplification Sensitivity by Addition of Hexaamminecobalt (III) Chloride With regard to each of DNA polymerases, the effects on the amplification sensitivity by the addition of hexaamminecobalt (III) chloride were examined.

The DNA polymerases used and the composition for the reaction mixture were similar to those in Example 17, except for the cationic complex, where in cases of using Taq DNA Polymerase and Pyrobest DNA Polymerase, hexaamminecobalt (III) chloride was added so as to have a final concentration of 100 µM, or in a case of using ExTaq DNA Polymerase, hexaamminecobalt (III) chloride was added so as to have a final concentration of 50 µM, respectively. Further, the amount of template DNA was added so as to be 1 pg, 5 pg, 10 pg, 100 pg, or 1 ng, respectively.

The reaction was carried out in Fast mode by using TaKaRa PCR Thermal Cycler Personal. The reaction conditions are as follows. When using Taq DNA Polymerase and Pyrobest DNA Polymerase, the reaction in 30 cycles was carried out, wherein one cycle of reaction comprises a process consisting of 98° C., 5 seconds—68° C., 2 minutes. When using ExTaq DNA Polymerase, the reaction in 30 cycles was carried out, wherein one cycle of reaction comprises a process consisting of 98° C., 5 seconds—68° C., 1 minute.

On the other hand, as a control, the reaction for one without addition of the cationic complex was carried out in the same manner.

After the termination of the reaction, 5 µl of each of the resulting reaction mixtures was subjected to electrophoresis on 2% agarose gel containing ethidium bromide in an amount of 0.00005%. The gel after the electrophoresis was subjected to ultraviolet irradiation to visualize the band ascribed to the amplified product, whereby an amplified fragment was confirmed.

As a result, there could be confirmed that in any case where any enzymes were used, the addition of hexaamminecobalt (III) chloride allowed to amplify even in an amount of template DNA of 1 pg, amplification can be carried out by. On the other hand, in the case of no addition, amplification could not be carried out just with an amount of template DNA of 1 pg.

EXAMPLE 20

Effects on Amplification Reaction in Low-Magnesium Concentration Reaction Mixture by Addition of Hexaamminecobalt (III) Chloride Using hexaamminecobalt (III) chloride, the effects on the amplification reaction in a reaction mixture having a magnesium concentration lower than that of a usually employed one were examined.

The DNA polymerases used and the composition for the reaction mixture were similar to those in Example 17, except for using each of magnesium-free, 10×PCR buffers (each being manufactured by Takara Shuzo Co., Ltd.) for each DNA polymerase. Further, with regard to magnesium chloride, magnesium chloride was added so as to have an amount smaller than the usual content for each of Taq DNA Polymerase (the amount being 0.75 mM against the usual amount of 1.5 mM), Pyrobest DNA Polymerase (the amount being 0.5 mM against the usual amount of 1 mM), or ExTaq DNA Polymerase (the amount being 1.25 mM against the usual amount of 2 mM). Further, with regard to the cationic complex, in cases of using Taq DNA Polymerase and Pyrobest DNA Polymerase, hexaamminecobalt (III) chloride was added so as to have a final concentration of 100 µM, or in a case of using ExTaq DNA Polymerase, hexaamminecobalt (III) chloride was added so as to have a final concentration of 10 µM, respectively.

The reaction was carried out in Fast mode by using TaKaRa PCR Thermal Cycler Personal. The reaction conditions are as follows. When using Taq DNA Polymerase and Pyrobest DNA Polymerase, the reaction in 30 cycles was carried out, wherein one cycle of reaction comprises a process consisting of 98° C., 5 seconds—68° C., 2 minutes. When using ExTaq DNA Polymerase, the reaction in 30 cycles was carried out, wherein one cycle of reaction comprises a process consisting of 98° C., 5 seconds—68° C., 1 minute.

On the other hand, the reaction for one without addition of the cationic complex was carried out in the same manner as a control.

After the termination of the reaction, 5 µl of the resulting reaction mixture was subjected to electrophoresis on 2% agarose gel containing ethidium bromide in an amount of 0.00005%. The gel after the electrophoresis was subjected to ultraviolet irradiation to visualize the band ascribed to the amplified product, whereby an amplified fragment was confirmed.

As a result, there was confirmed that in all of DNA polymerases, the addition of the cationic complex allowed to amplify in a case where the magnesium concentration was made smaller than the usual content. However, in the case of no addition of cationic complex, amplification could not be carried out.

EXAMPLE 21

Effects of Low-Primer Concentration in Reaction Mixture on Amplification Reaction by Addition of Hexaamminecobalt (III) Chloride Using hexaamminecobalt (III) chloride, the effects of a reaction mixture having a primer concentration lower than that of a usually employed one on the amplification reaction were examined.

The DNA polymerases used and the composition for the reaction mixture were similar to those in Example 17, except for adding two kinds of primers used each in an amount of 2, 2.5, 3.3, 5, 10 or 20 pmol, respectively. Further, with regard to the cationic complex, in cases of using Taq DNA Polymerase and Pyrobest DNA Polymerase, hexaamminecobalt (III) chloride was added so as to have a final concentration of 100 µM, or in a case of using ExTaq DNA Polymerase, hexaamminecobalt (III) chloride was added so as to have a final concentration of 50 µM, respectively.

The reaction was carried out in Fast mode by using TaKaRa PCR Thermal Cycler Personal. The reaction conditions are as follows. When using Taq DNA Polymerase and Pyrobest DNA Polymerase, the reaction in 30 cycles was carried out, wherein one cycle of reaction comprises a process consisting of 98° C., 5 seconds—68° C., 2 minutes. When using ExTaq DNA Polymerase, the reaction in 30 cycles was carried out, wherein one cycle of reaction comprises a process consisting of 98° C., 5 seconds—68° C., 1 minute.

On the other hand, the reaction for one without addition of the cationic complex was carried out in the same manner as a control.

After the termination of the reaction, 5 µl of each of the resulting reaction mixtures was subjected to electrophoresis on 2% agarose gel containing ethidium bromide in an amount of 0.00005%. The gel after the electrophoresis was subjected to ultraviolet irradiation to visualize the band ascribed to the amplified product, whereby an amplified fragment was confirmed.

As a result, there was confirmed that in a case of using Taq DNA Polymerase, a fragment can be amplified even with a primer amount of as little as 2 pmol in the presence of the cationic complex. On the other hand, in the case of no addition of the cationic complex, amplification could not be carried out. Next, in a case of using Pyrobest DNA Polymerase, a fragment can be amplified even with a primer amount of as little as 3.3 pmol in the presence of the cationic complex. On the other hand, in the case of no addition of the cationic complex, amplification could not be carried out. Further, in a case of using ExTaq DNA Polymerase, a fragment can be amplified even with a primer amount of as little as 2.5 pmol in the presence of the cationic complex. On the other hand, in the case of no addition of the cationic complex, amplification could not be carried out.

EXAMPLE 22

Effects on Enzyme Amount and Amplification Reactions by Addition of Hexaamminecobalt (III) Chloride Using hexaamminecobalt (III) chloride, the effects on amplification reaction with an enzyme in an amount of one-half that of usually used.

As the enzymes, Taq DNA Polymerase and ExTaq DNA Polymerase were used.

The composition for the reaction mixture was similar to those in Example 17, except for the amount of DNA polymerase used. In other words, 0.625 U of DNA polymerase was used. Further, with regard to the cationic complex, in cases of using Taq DNA Polymerase and Pyrobest DNA Polymerase, hexaamminecobalt (III) chloride was added so as to have a final concentration of 100 μM, or in a case of using ExTaq DNA Polymerase, hexaamminecobalt (III) chloride was added so as to have a final concentration of 50 μM, respectively.

The reaction was carried out in Fast mode by using TaKaRa PCR Thermal Cycler Personal. The reaction conditions are as follows. When using Taq DNA Polymerase, the reaction in 30 cycles was carried out, wherein one cycle of reaction comprises a process consisting of 98° C., 5 seconds—68° C., 2 minutes. When using ExTaq DNA Polymerase, the reaction in 30 cycles was carried out, wherein one cycle of reaction comprises a process consisting of 98° C., 5 seconds—68° C., 1 minute.

On the other hand, as a control, the reaction for one using 1.25 U of DNA polymerase without addition of the cationic complex was carried out in the same manner.

After the termination of the reaction, 5 μl of each of the resulting reaction mixtures was subjected to electrophoresis on 2% agarose gel containing ethidium bromide in an amount of 0.00005%. The gel after the electrophoresis was subjected to ultraviolet irradiation to visualize the band ascribed to the amplified product, whereby an amplified fragment was confirmed.

As a result, there was confirmed that in either case of using Taq DNA Polymerase or ExTaq DNA Polymerase, even if the amount is one-half the usual amount, the fragment can be amplified in the presence of the cationic complex to almost the same level as the usually used amount of the case of no addition.

EXAMPLE 23

Effects on Addition of Cationic Complex When Amplifying GC-Rich Region

The effects on addition of the cationic complex were examined when PCR amplification was carried out with a GC-rich region as a target. As the cationic complex, there was used tris(ethylenediamine)cobalt (III) chloride, or tris(ethylenediamine)rhodium (III) trichloride•trihydrate. Template DNA was prepared from HT29 cells by conventional method. Amplified region and amplified chain lengths were human ApoE genomic region and 441 bp. The GC content of this amplified region was about 74%. As DNA polymerase, TaKaRa LA-Taq DNA Polymerase (manufactured by Takara Shuzo Co., Ltd., hereinafter referred to as "LA-Taq DNA Polymerase") was used. The composition for a reaction mixture is shown below.

Composition for Reaction Mixture:
25 μl of 2×GC buffer I (manufactured by Takara Shuzo Co., Ltd.), 0.4 mM each of dATP, dCTP, dGTP and dTTP, 2.5 U of LA-Taq DNA Polymerase, 100 ng of HT29 cells genomic region, and 20 pmol each of primers ApoE-1 and ApoE-2 (a final volume being 50 μl). Each of the above cationic complex was added to the above reaction mixture so as to have a final concentration of 50, 100, 200, or 500 μM, respectively.

The reaction was carried out in Fast mode by using TaKaRa PCR Thermal Cycler Personal. As regarding the reaction conditions, the reaction in 30 cycles was carried out, wherein one cycle of reaction comprises a process consisting of 98° C., 5 seconds—64° C., 10 seconds—72° C., 40 seconds. On the other hand, as a control, the reaction for one without addition of the cationic complex was carried out in the same manner.

After the termination of the reaction, 5 μl of each of the resulting reaction mixtures was subjected to electrophoresis on 2% agarose gel containing ethidium bromide in an amount of 0.00005%. The gel after the electrophoresis was subjected to ultraviolet irradiation to visualize the band ascribed to the amplified product, whereby an amplified fragment was confirmed.

As a result, in a case of adding tris(ethylenediamine)cobalt (III) chloride, there was confirmed that the DNA synthesis reaction was enhanced as the concentration of added complex was increased. In addition, in a case of adding tris(ethylenediamine)rhodium (III) trichloride•trihydrate, there was also confirmed that the DNA synthesis reaction was enhanced as the concentration of added complex was increased as 100 μM, 200 μM and 500 μM. However, in the case of no addition for neither of the cationic complexes, amplification could not be carried out.

EXAMPLE 24

Effects on Amplified Chain Length When Adding Cationic Complex

The effects on the amplified chain length when adding a cationic complex were examined. As the cationic complex, there was used hexaamminecobalt (III) trichloride. As template DNA, there was used *Escherichia coli* genome or λDNA. As primers, in cases of using Taq DNA Polymerase and Pyrobest DNA Polymerase, there was used a combination of Eco1 and Eco5, and in a case of using LA-Taq DNA Polymerase, there was used a combination of λL36 and λR485. As DNA polymerase, there was used Taq DNA Polymerase, Pyrobest DNA Polymerase or LA-Taq DNA Polymerase. The composition for the reaction mixture was similar to those in Example 17, except for using the above primer pairs and 10 ng of *Escherichia coli* genome as template DNA in cases of using Taq DNA Polymerase and Pyrobest DNA Polymerase. To the above reaction mixture was added hexaamminecobalt (III) trichloride so as to have a final concentration of 10 μM or 20 μM in a case of using Taq DNA Polymerase, or was added hexaamminecobalt (III) trichloride so as to have a final concentration of 50 μM or 100 μM in a case of using Pyrobest DNA Polymerase, respectively. As a control, the one without addition of the cationic complex was also prepared in the same manner.

On the other hand, the composition for a reaction mixture when using LA-Taq DNA Polymerase is shown below.

5 µl of 10×LA-PCR Buffer II ($Mg^{2+}$ plus) (manufactured by Takara Shuzo Co., Ltd.), 0.4 mM each of dATP, dCTP, dGTP and dTTP, 2.5 U of LA-Taq DNA Polymerase, 1 ng of λDNA, and 20 pmol each of primers λL36 and λR485 (a final volume being 50 µl). Hexaamminecobalt (III) trichloride was added to the above reaction mixture so as to have a final concentration of 50 µM. As a control, the one without addition of the cationic complex was also prepared in the same manner.

The reaction was carried out in Fast mode by using TaKaRa PCR Thermal Cycler Personal. The reaction conditions are as follows. When using Taq DNA Polymerase and Pyrobest DNA Polymerase, the reaction in 30 cycles was carried out, wherein one cycle of reaction comprises a process consisting of 98° C., 5 seconds—68° C., 10 minutes. When using LA-Taq DNA Polymerase, after treating at 94° C., 1 minute, the reaction in 30 cycles was carried out, wherein one cycle of reaction comprises a process consisting of 98° C., 10 seconds—68° C., 15 minutes, and thereafter the reaction was completed by treating at 72° C., 15 minutes.

After the termination of the reaction, 5 µl of each of the resulting reaction mixtures was subjected to electrophoresis on 2% agarose gel containing ethidium bromide in an amount of 0.00005%. The gel after the electrophoresis was subjected to ultraviolet irradiation to visualize the band ascribed to the amplified product, whereby an amplified fragment was confirmed.

As a result, when using Taq DNA Polymerase, a desired DNA fragment could be excellently amplified even when hexaamminecobalt (III) trichloride was added at any of concentrations. However, in the case of no addition, a fragment was only slightly amplified. Next, when using Pyrobest DNA Polymerase, a desired DNA fragment could be excellently amplified even when hexaamminecobalt (III) trichloride was added at any of concentrations. However, in the case of no addition, a fragment was only slightly amplified. Further, when using LA-Taq DNA Polymerase, a desired DNA fragment could be excellently amplified even when hexaamminecobalt (III) trichloride was added at any of concentrations. However, in the case of no addition, a fragment was only slightly amplified.

INDUSTRIAL APPLICABILITY

According to the present invention, there is provided a DNA synthesis reaction-enhancer which enhances DNA synthesis reaction by DNA polymerase. The enhancer exhibits an action for various kinds of DNA polymerases, and enhances the DNA synthesis reaction. In addition, the present invention provides a DNA synthesis reaction composition which is capable of carrying out DNA synthesis at high efficiency. The DNA synthesis reaction-enhancer and the DNA synthesis reaction composition of the present invention can be utilized for various processes using DNA polymerases, for instance, PCR method, and can be utilized for research agents for genetic engineering.

The invention claimed is:

1. A DNA synthesis reaction composition comprising:
   1) a DNA polymerase having 3'→5' exonuclease activity;
   2) water-soluble acidic macromolecular substances selected from the group consisting of κ-carrageenan, dermatan sulfate, hyaluronic acid, polyvinyl sulfates, polystyrene sulfates, sodium polyglutamate, polyacrylic acids, and water-soluble salts thereof; and
   3) components necessary for DNA synthesis using DNA polymerase.

2. The DNA synthesis reaction composition according to claim 1, wherein the composition comprises two or more kinds of DNA polymerases.

3. The DNA synthesis reaction composition according to claim 2, wherein the composition comprises one DNA polymerase having 3'→5' exonuclease activity, and one DNA polymerase having no 3'→5' exonuclease activity.

4. A method for synthesizing DNA comprising steps of:
   a) preparing a reaction mixture by using the DNA synthesis composition of any one of claims 1 to 3; and
   b) reacting a DNA synthesis.

5. A kit for use in in vitro DNA synthesis, comprising:
   1) DNA polymerases having 3'→5' exonuclease activity;
   2) water-soluble acidic macromolecular substances selected from the group consisting of κ-carrageenan, dermatan sulfate, hyaluronic acid, polyvinyl sulfates, polystyrene sulfates, sodium polyglutamate, polyacrylic acids, and water-soluble salts thereof; and
   3) components necessary for DNA synthesis using DNA polymerase.

6. The kit according to claim 5, wherein the kit comprises two or more kinds of DNA polymerases.

7. The kit according to claim 6, wherein the kit comprises one DNA polymerase having 3'→5' exonuclease activity, and one DNA polymerase having no 3'→5' exonuclease activity.

8. A DNA synthesis reaction composition comprising:
   1) a DNA polymerase having 3'→5' exonuclease activity;
   2) a water-soluble acidic macromolecular substance; and
   3) components necessary for DNA synthesis using DNA polymerase,
wherein the water-soluble acidic macromolecular substance is sodium polyacrylate.

9. A DNA synthesis reaction composition comprising:
   1) a DNA polymerase having 3'→5' exonuclease activity;
   2) a water-soluble acidic macromolecular substance; and
   3) components necessary for DNA synthesis using DNA polymerase,
wherein the water-soluble acidic macromolecular substance is sodium polyglutamate.

10. A kit for use in in vitro DNA synthesis, comprising:
    1) DNA polymerases having 3'→5' exonuclease activity;
    2) a water-soluble acidic macromolecular substance; and
    3) components necessary for DNA synthesis using DNA polymerase,
wherein the water-soluble acidic macromolecular substance is sodium polyacrylate.

11. A kit for use in in vitro DNA synthesis, comprising:
    1) DNA polymerases having 3'→5' exonuclease activity;
    2) a water-soluble acidic macromolecular substance; and
    3) components necessary for DNA synthesis using DNA polymerase,
wherein the water-soluble acidic macromolecular substance is sodium polyglutamate.

* * * * *

SEQUENCE LISTING

```
<160> NUMBER OF SEQ ID NOS: 18

<210> SEQ ID NO 1
<211> LENGTH: 23
<212> TYPE: DNA
<213> ORGANISM: Artificial Sequence
<220> FEATURE:
<223> OTHER INFORMATION: Synthetic primer derived from bacteriophage
      lambda

<400> SEQUENCE: 1
gatgagttcg tgtccgtaca act                                              23

<210> SEQ ID NO 2
<211> LENGTH: 22
<212> TYPE: DNA
<213> ORGANISM: Artificial Sequence
<220> FEATURE:
<223> OTHER INFORMATION: Synthetic primer derived from bacteriophage
      lambda

<400> SEQUENCE: 2
acaaagccag ccggaatatc tg                                               22

<210> SEQ ID NO 3
<211> LENGTH: 35
<212> TYPE: DNA
<213> ORGANISM: Artificial Sequence
<220> FEATURE:
<223> OTHER INFORMATION: Synthetic primer derived from bacteriophage
      lambda

<400> SEQUENCE: 3
```

```
gatgagttcg tgtccgtaca actggcgtaa tcatg                              35
```

<210> SEQ ID NO 4
<211> LENGTH: 25
<212> TYPE: DNA
<213> ORGANISM: Artificial Sequence
<220> FEATURE:
<223> OTHER INFORMATION: Synthetic primer derived from bacteriophage
      lambda

<400> SEQUENCE: 4

```
ggttatcgaa atcagccaca gcgcc                                         25
```

<210> SEQ ID NO 5
<211> LENGTH: 23
<212> TYPE: DNA
<213> ORGANISM: Artificial Sequence
<220> FEATURE:
<223> OTHER INFORMATION: Synthetic primer derived from bacteriophage
      lambda

<400> SEQUENCE: 5

```
gcgtaccttt gtctcacggg caa                                           23
```

<210> SEQ ID NO 6
<211> LENGTH: 22
<212> TYPE: DNA
<213> ORGANISM: Artificial Sequence
<220> FEATURE:
<223> OTHER INFORMATION: Synthetic primer derived from bacteriophage
      lambda

<400> SEQUENCE: 6

```
gatagctgtc gtcataggac tc                                            22
```

<210> SEQ ID NO 7
<211> LENGTH: 23
<212> TYPE: DNA
<213> ORGANISM: Artificial Sequence
<220> FEATURE:
<223> OTHER INFORMATION: Synthetic primer derived from bacteriophage
      lambda

<400> SEQUENCE: 7

```
cttaaccagt gcgctgagtg act                                           23
```

<210> SEQ ID NO 8
<211> LENGTH: 28
<212> TYPE: DNA
<213> ORGANISM: Artificial Sequence
<220> FEATURE:
<223> OTHER INFORMATION: Synthetic primer derived from bacteriophage
      lambda

<400> SEQUENCE: 8

```
ttgccacttc cgtcaaccag gcttatca                                      28
```

<210> SEQ ID NO 9
<211> LENGTH: 29
<212> TYPE: DNA
<213> ORGANISM: Artificial Sequence
<220> FEATURE:
<223> OTHER INFORMATION: Synthetic primer derived from bacteriophage
      lambda

<400> SEQUENCE: 9

```
tgtccgtcag ctcataacgg tacttcacg                                     29
```

```
<210> SEQ ID NO 10
<211> LENGTH: 28
<212> TYPE: DNA
<213> ORGANISM: Artificial Sequence
<220> FEATURE:
<223> OTHER INFORMATION: Synthetic primer derived from bacteriophage
      lambda

<400> SEQUENCE: 10
atatctggcg gtgcaatatc ggtactgt                                            28

<210> SEQ ID NO 11
<211> LENGTH: 28
<212> TYPE: DNA
<213> ORGANISM: Artificial Sequence
<220> FEATURE:
<223> OTHER INFORMATION: Synthetic primer derived from bacteriophage
      lambda

<400> SEQUENCE: 11
gacaatctgg aatacgccac ctgacttg                                            28

<210> SEQ ID NO 12
<211> LENGTH: 36
<212> TYPE: DNA
<213> ORGANISM: Artificial Sequence
<220> FEATURE:
<223> OTHER INFORMATION: Synthetic primer derived from bacteriophage
      lambda

<400> SEQUENCE: 12
gggcggcgac ctcgcgggtt ttcgctattt atgaaa                                   36

<210> SEQ ID NO 13
<211> LENGTH: 36
<212> TYPE: DNA
<213> ORGANISM: Artificial Sequence
<220> FEATURE:
<223> OTHER INFORMATION: Synthetic primer derived from bacteriophage
      lambda

<400> SEQUENCE: 13
taacctgtcg gatcaccgga aaggacccgt aaagtg                                   36

<210> SEQ ID NO 14
<211> LENGTH: 35
<212> TYPE: DNA
<213> ORGANISM: Artificial Sequence
<220> FEATURE:
<223> OTHER INFORMATION: Artificial Sequence Primer derived from
      Escherichia coli

<400> SEQUENCE: 14
ggtggcgatg caaatgcaat cttcgttgcc ccaac                                    35

<210> SEQ ID NO 15
<211> LENGTH: 35
<212> TYPE: DNA
<213> ORGANISM: Artificial Sequence
<220> FEATURE:
<223> OTHER INFORMATION: Artificial Sequence Primer derived from
      Escherichia coli

<400> SEQUENCE: 15
ttatgtatgc cgcgtatcag cttcatgtct ggctc                                    35

<210> SEQ ID NO 16
```

-continued

```
<211> LENGTH: 35
<212> TYPE: DNA
<213> ORGANISM: Artificial Sequence
<220> FEATURE:
<223> OTHER INFORMATION: Artificial Sequence Primer derived from
      Escherichia coli

<400> SEQUENCE: 16
atcatctaac ctgttctgga aaacgcttgc gcagc                              35

<210> SEQ ID NO 17
<211> LENGTH: 19
<212> TYPE: DNA
<213> ORGANISM: Artificial Sequence
<220> FEATURE:
<223> OTHER INFORMATION: Artificial Sequence Primer derived from Homo
      sapiens

<400> SEQUENCE: 17
aagcgcctgg cagtgtacc                                                19

<210> SEQ ID NO 18
<211> LENGTH: 21
<212> TYPE: DNA
<213> ORGANISM: Artificial Sequence
<220> FEATURE:
<223> OTHER INFORMATION: Artificial Sequence Primer derived from Homo
      sapiens

<400> SEQUENCE: 18
cttcggcgtt cagtgattgt c                                             21
```